US011421205B2

(12) United States Patent
Birikh et al.

(10) Patent No.: US 11,421,205 B2
(45) Date of Patent: Aug. 23, 2022

(54) ALKALINE LACCASE VARIANTS WITH IMPROVED PROPERTIES

(71) Applicant: METGEN OY, Kaarina (FI)

(72) Inventors: Klara Birikh, Kaarina (FI); Veera Kaarina Hämäläinen, Kaarina (FI)

(73) Assignee: Metgen OY, Kaarina (FI)

( * ) Notice: Subject to any disclaimer, the term of this patent is extended or adjusted under 35 U.S.C. 154(b) by 0 days.

(21) Appl. No.: 16/963,964

(22) PCT Filed: Jan. 22, 2019

(86) PCT No.: PCT/EP2019/051484
§ 371 (c)(1),
(2) Date: Jul. 22, 2020

(87) PCT Pub. No.: WO2019/145288
PCT Pub. Date: Aug. 1, 2019

(65) Prior Publication Data
US 2021/0002617 A1    Jan. 7, 2021

(30) Foreign Application Priority Data
Jan. 23, 2018  (EP) .................................. 18152993

(51) Int. Cl.
*C12N 9/02*      (2006.01)
(52) U.S. Cl.
CPC .... *C12N 9/0061* (2013.01); *C12Y 110/03002* (2013.01)
(58) Field of Classification Search
CPC .................................................. C12N 9/0061
See application file for complete search history.

(56) References Cited

U.S. PATENT DOCUMENTS 10,190,102 B2 * 1/2019 Birikh .................. C12N 9/0061
10,626,553 B2 * 4/2020 Birikh .................... D21C 9/153

FOREIGN PATENT DOCUMENTS

| WO | 2015144679 A1 | 10/2015 |
| WO | 2015155363 A1 | 10/2015 |
| WO | 2017102542 A1 | 6/2017 |
| WO | WO 2015/158803 | * 10/2019 |

OTHER PUBLICATIONS

Studer. Residue mutations and their impact on protein structure and function: detecting beneficial and pathogenic changes. Biochem. J. (2013) 449, 581-594.*
Al-Kahem Al-Balawi, Thamir, et al. "*Anoxybacillus* Sp. Strain UARK-01, a New Thermophilic Soil Bacterium with Hyperthermostable Alkaline Laccase Activity." Current Microbiology, vol. 74, No. 6, 2017, pp. 762-771.
Database EMBL [Online] Accession No. W4PYT0, Mar. 19, 2014, "Spore Coate Protein A", XP002780263, GAE24845.1 ECO: 0000313, UniProt Mar. 19, 2014, XP002780263, 1 page.
Kumar, S. V. Suresh, et al. "Combined Sequence and Structure Analysis of the Fungal Laccase Family." Biotechnology and Bioengineering, vol. 83, No. 4, 2003, pp. 386-394.
PCT International Search Report and Written Opinion; Application No. PCT/EP2019/051484, International filing date of Jan. 22, 2019, Metgen OY, ISA European Patent Office, Authorized Officer Alain Ury, dated Mar. 13, 2019, 11 pages.
Vasina, D, et al. "The Trametes Hirsuta 072 Laccase Multigene Family: Genes Identification and Transcriptional Analysis under Copper Ions Induction." Biochimie, vol. 116, 2015, pp. 154-164.

* cited by examiner

*Primary Examiner* — Yong D Pak
(74) *Attorney, Agent, or Firm* — Patent Law Works, LLP

(57) ABSTRACT

The present invention relates to laccase variants and uses thereof as eco-friendly biocatalysts in various industrial processes. More in particular, the invention relates to a polypeptide with laccase activity comprising an amino acid sequence that is at least 90% identical to the amino acid sequence according to SEQ ID NO: 1, wherein the polypeptide comprises at least one amino acid selected from the group consisting of Alanine, Proline, Aspartic acid, Isoleucine, Proline, Proline, Threonine and Proline at a position corresponding to of positions 253, 128, 384, 364, 292, 450, 33 and 322 in SEQ ID NO: 1 respectively.

20 Claims, No Drawings
Specification includes a Sequence Listing.

ALKALINE LACCASE VARIANTS WITH IMPROVED PROPERTIES

FIELD OF THE INVENTION

The present invention relates to laccase variants and uses thereof as eco-friendly biocatalysts in various industrial processes. More in particular, the invention provides variant alkaline laccases that have an increased yield when expressed in a heterologous or recombinant expression system. It also provides means and methods for their production and use.

BACKGROUND OF THE INVENTION

Laccases (EC 1.10.3.2) are enzymes having a wide taxonomic distribution and belonging to the group of multicopper oxidases. Laccases are eco-friendly catalysts, which use molecular oxygen from air to oxidize various phenolic and non-phenolic lignin-related compounds as well as highly recalcitrant environmental pollutants, and produce water as the only side-product. These natural "green" catalysts are used for diverse industrial applications including the detoxification of industrial effluents, mostly from the paper and pulp, textile and petrochemical industries, use as bioremediation agent to clean up herbicides, pesticides and certain explosives in soil. Laccases are also used as cleaning agents for certain water purification systems. In addition, their capacity to remove xenobiotic substances and produce polymeric products makes them a useful tool for bioremediation purposes. Another large proposed application area of laccases is biomass pretreatment in the biofuel industry and pulp and paper industry.

Laccase molecules are usually monomers consisting of three consecutively connected cupredoxin-like domains twisted in a tight globule. The active site of laccases contains four copper ions: a mononuclear "blue" copper ion (T1 site) and a three-nuclear copper cluster (T2/T3 site) consisting of one T2 copper ion and two T3 copper ions.

Laccases may be isolated from different sources such as plants, fungi or bacteria and are very diverse with respect to their primary sequences. However, they have some conserved regions in the sequences and certain common features in their three-dimensional structures. A comparison of sequences of more than 100 laccases has revealed four short conservative regions (no longer than 10 aa each) which are specific for all laccases [7, 8] One cysteine and ten histidine residues form a ligand environment for copper ions of the laccase active site present in these four conservative amino acid sequences.

The best studied bacterial laccase is CotA laccase (CotA). CotA is a component of the outer coat layers of *bacillus* endospore. It is a 65-kDa protein encoded by the cotA gene [1].

CotA belongs to a diverse group of multi-copper "blue" oxidases that includes the laccases. This protein demonstrates high thermostability, and resistance to various hazardous elements in accordance with the survival abilities of the bacterial endospore.

Recombinant protein expression in easily cultivatable hosts allows higher productivity in shorter time and reduces the costs of production. The versatility and scaling-up possibilities of the recombinant protein production opened up new commercial opportunities for their industrial uses. Moreover, proteins from pathogenic or toxin-producing species can advantageously produced in safer or even GRAS (generally recognized as safe) microbial hosts. In addition, protein engineering can be employed to improve the stability, activity and/or specificity of an enzyme, thus tailor-made enzymes can be produced to suit the requirement of the users or of the process.

Enzyme productivity can be increased by the use of multiple gene copies, strong promoters and efficient signal sequences, properly designed to address proteins to the extracellular medium, thus simplifying downstream processing.

Recombinant protein yield in bacterial hosts is often limited by the inability of the protein to fold into a correct 3D-structure upon biosynthesis of the polypeptide chain. This may cause exposure of hydrophobic patches on the surface of the protein globule and result in protein aggregation. Mechanisms of heterologous protein folding in vivo are poorly understood, and foldability of different proteins in bacteria is unpredictable.

Yield of soluble active protein can be sometimes improved by changing cultivation conditions. In addition, there are examples when protein yield was improved by introducing single point mutations in the protein sequence. However, no rational has yet been identified behind finding suitable mutations.

Heterologous expression of laccases in *Escherichia coli* has been often used as a strategy to get around the problem of obtaining laccases that are not easily producible in natural hosts. The recombinant expression of *Bacillus subtilis* CotA in *E. coli* has allowed its deep characterization, structure solving, and functional evolution [1,2,3]. However, very often the production yield is extremely low, due to a strong tendency of this enzyme to form aggregates which renders the protein irreversibly inactive [4]. This tendency has been attributed to the fact that in nature COTA laccase is integrated in a spore coat structure via interaction with other protein components, and it is likely that correct laccase folding is enhanced by interaction with other proteins. When this laccase is recombinantly expressed as an individual polypeptide, those supporting interactions are missing and many misfolded proteins form aggregates in bacterial cells. When expressed in higher microorganisms such as yeast, misfolded laccase molecules are degraded for a large part.

There is a need in the art for means and methods for improving the yield of laccases in heterologous expression systems. This is particularly true for bacterial laccases.

SUMMARY OF THE INVENTION

The present invention addresses this need in that it provides variant laccases such as alkaline laccases with improved properties. More in particular, it provides variants of a *Bacillus wakoensis* alkaline laccase according to SEQ ID NO:1 or its analogues. These variant laccases share the technical feature that they have an improved yield when expressed in a recombinant host such as *E. coli* as compared to the yield of a wild type polypeptide according to SEQ ID NO: 1.

Even more in particular, the invention relates to a polypeptide with laccase activity (EC 1.10.3.2) comprising an amino acid sequence that is at least 90% identical to the amino acid sequence according to SEQ ID NO: 1, wherein the polypeptide comprises at least one amino acid selected from the group consisting of:

Alanine at a position corresponding to position 253 in SEQ ID NO: 1,

Proline at a position corresponding to position 128 in SEQ ID NO: 1,

Aspartic acid at a position corresponding to position 384 in SEQ ID NO: 1,

Isoleucine at a position corresponding to position 364 in SEQ ID NO: 1,

Proline at a position corresponding to position 292 in SEQ ID NO: 1,

Proline at a position corresponding to position 450 in SEQ ID NO: 1,

Threonine at a position corresponding to position 33 in SEQ ID NO: 1 and

Proline at a position corresponding to position 322 in SEQ ID NO: 1.

In addition, the invention provides compositions comprising the above polypeptides, as well as improved nucleic acids, vectors and compositions comprising such nucleic acids encoding the laccase enzymes according to the invention.

The invention also provides recombinant heterologous expression systems such as host cells comprising a nucleic acid, a vector or a composition according to the invention.

The invention also provides a method for producing a polypeptide according to the invention, comprising the steps of:
a. culturing a recombinant host cell under conditions suitable for the production of the polypeptide, and
b. recovering the polypeptide obtained, and
c. optionally purifying the polypeptide.

The invention also provides the use of a polypeptide as described herein in an application selected from the group consisting of pulp delignification, oxidation of lignin, degrading or decreasing the structural integrity of lignocellulosic material, textile dye bleaching, wastewater detoxification, xenobiotic detoxification, production of a sugar from a lignocellulosic material and recovering cellulose from a biomass.

The invention also provides a method for improving the yield of a polypeptide with laccase activity in a heterologous expression system comprising the step of altering at least one amino acid at a position selected from the group consisting of positions corresponding to positions 253, 128, 384, 364, 292, 450, 33 and 322 in SEQ ID NO: 1 into an Alanine, Proline, Aspartic acid, Isoleucine, Proline, Proline, Threonine and Proline respectively, wherein the polypeptide with laccase activity is a polypeptide with an amino acid sequence according to SEQ ID NO: 1 or a polypeptide with an amino acid sequence that is at least 90% identical to the sequence of SEQ ID NO: 1.

Preferred embodiments of these aspects will be described in more detail below. For the purpose of clarity and a concise description, features are described herein as part of the same or separate embodiments, however, it will be appreciated that the scope of the invention may include embodiments having combinations of all or some of the features described.

DETAILED DESCRIPTION OF THE INVENTION

Bacterial laccases have been described to oxidize phenolic compounds in alkaline conditions. We have therefore tested several of such laccases and found that all of them were rather unstable in solution at high alkaline pH (such as pH 9-11) and elevated temperatures (such as 40-70 degrees C.).

The bacterial laccases initially tested herein were from *Bacillus wakoensis* (SEQ ID NO: 1), *B. clausii* (SEQ ID NO: 65), *B. subtilis* (SEQ ID NO: 66) and *Escherichia coli* (SEQ ID NO: 67). Although all of these bacterial laccases showed some initial activity at pH 9-11, they appeared to be highly unstable under this condition, especially at elevated temperatures such as 40-70 degrees Celsius. This was concluded from the fact that they lost 80% of their activity after one hour of incubation at pH 11 at 70 degrees C. in buffer and 60% of their activity after one hour of incubation at pH 9 at 40 degrees C. in buffer.

We then tested several other known bacterial laccases with Accession Numbers YP_003865004.1, WP_004397739.1, WP_019713492.1, AGR50961.1, YP_007425830.1, YP_004206641.1, YP_006230497.1, EXF51833.1, WP_003234000.1, YP_006628799.1, NP_388511.1, YP_007661398.1, ACS44284.1, AGK12417.1, AFN66123.1, ACM46021.1, WP_010329056.1, AEK80414.1, WP_010333230.1, AAB62305.1, YP_003972023.1, WP_010787813.1, WP_007609818.1, YP_007496315.1, YP_005419918.1, YP_007185316.1, YP_001420286.1, ADZ57286.1, WP_007408880.1, WP_021495201.1, AHK48246.1, YP_003919218.1, WP_016937040.1, WP_006637314.1, WP_008344352.1, WP_007496963.1, WP_017359847.1, AEX93437.1, WP_003213818.1, AFL56752.1, WP_019743779.1, AFK33221.1, YP_001485796.1, WP_008355710.1, WP_023855578.1, YP_008076901.1, AFP45763.1, WP_003179495.1, YP_077905.1, EWH20929.1, WP_017796468.1, WP_018661628.1, NP_692267.1, WP_017553860.1 and WP_019721501.1. These Accession Numbers refer to proteins in the database of the National Center of Biotechnology Information at the US National Library of Medicine at National institute of Health (https://www.ncbi.nlm.nih.gov/protein/).

We found that every enzyme tested lost more than 50% of its activity after one hour of incubation at pH 11 and 70 degrees Celsius. Total loss of activity was observed after 3-4 hours of incubation at these conditions for all laccases tested. It may therefore be easily concluded that bacterial laccases are not suitable for prolonged use at an alkaline pH, such as a pH of 9-11.

Surprisingly however, we found that a particular laccase (according to SEQ ID NO: 1, obtained from *Bacillus wakoensis*), although quickly inactivated when tested in a buffered solution at high temperature and alkaline pH, was remarkably stable at pH 9-11 and at 40-70 degrees Celsius in the presence of lignin or lignocellulosic material such as pulp, more in particular wood pulp.

In more detail, we found that it retained 70% of its activity after treatment at pH 11 at 70 degrees Celsius for 3 hours in wood pulp, whereas the enzymes from *B. clausii* (SEQ ID NO: 65), *B. subtilis* (SEQ ID NO: 66) and *Escherichia coli* (SEQ ID NO: 67) retained less than 20% of their activity under these conditions. The same phenomenon was observed at pH 9 and 40 degrees Celsius. The enzyme according to SEQ ID NO: 1 retained over 80% of its activity after treatment at pH 9 and 40 degrees Celsius for 4 hours in wood pulp, whereas the enzymes from *B. clausii* (SEQ ID NO: 65), *B. subtilis* (SEQ ID NO: 66) and *Escherichia coli* (SEQ ID NO: 67) retained less than 20% of their activity under these conditions So whereas the alkaline laccase according to SEQ ID NO: 1 or its analogues is equally suitable as any other alkaline laccase in any known process for laccases, such as a use selected from the group consisting of textile dye bleaching, wastewater detoxification, xenobiotic detoxification and recovering cellulose from a biomass, the enzyme is particularly suited for the process of lignin depolymerization at high pH and high temperature, such as a process selected from the group consisting of oxidation of lignin, degrading or decreasing the structural integrity of lignocellulosic material and production of a sugar from a lignocellulosic material.

Hence, a method is disclosed herein comprising an enzymatic treatment step of contacting lignin with a laccase in a solution or suspension at alkaline pH, wherein the laccase has an amino acid sequence according to SEQ ID NO: 1 or an amino acid sequence at least 90% identical to SEQ ID NO: 1 and wherein the lignin is depolymerized.

This finding also opens up the possibility to use this enzyme and its analogues for delignifying and/or bleaching of pulp at alkaline pH.

As used herein, the term "delignifying" refers to a process wherein the lignin in lignin-containing material is degraded or depolymerized resulting in a lower molecular weight of the lignin and an increased solubility of the lignin.

Hence, the present disclosure also provides a method for delignifying and/or bleaching of a pulp, comprising an enzymatic treatment step wherein lignin-containing pulp and a laccase are reacted at alkaline pH, wherein the laccase has an amino acid sequence according to SEQ ID NO: 1 or an amino acid sequence at least 90% identical to SEQ ID NO: 1.

As used herein, the term "pulp" is intended to mean a composition comprising lignocellulosic fibrous material prepared by chemically and/or mechanically separating cellulose fibers from wood, fiber crops or waste paper. Pulp is characterized by its ability to absorb water, which can be measured in milliliters as Canadian Standard Freeness (CSF). Pulp is also characterized by the amount of residual lignin, which can be expressed as Kappa number. The Kappa number is a measurement of standard potassium permanganate solution that the pulp will consume, which is determined by a standard protocol ISO 302. Kappa number has a range from 1 to 100, the less lignin, the lower the number. Delignification of lignocellulosic material can be characterized by a decrease in the kappa number. Wood pulp is the most common raw material in papermaking.

The term lignocellulosic material refers to a material that comprises (1) cellulose, hemicellulose, or a combination thereof and (2) lignin. The term "purified lignin" is used herein to indicate a dry matter content of 40% or above. This means that when the solution or suspension containing lignin as described above, is fully dried, 40% or more of the remaining dry matter is lignin.

The fact that the stabilizing effect of lignin on the laccase according to SEQ ID NO: 1 could be observed in pulp with a lignin content of 40% as well as with highly purified lignin with a lignin content of about 96%, shows that the stabilizing effect of lignin on the laccase according to SEQ ID NO: 1 is to be expected over a wide range dry-matter content of lignin-containing solutions or suspensions.

The stabilizing effect of lignin was also found over a wide concentration range of lignin. It was found in spruce pulp containing 0.5 grams of lignin per liter, as well as in a solution or suspension containing 2.2 grams of purified lignin per liter. It even appeared that the higher the concentration of lignin, the higher the stabilizing effect was.

The laccase according to SEQ ID NO: 1 is preferably produced in *Escherichia coli*. However, when expressed in *E. coli*, the yield of the enzyme according to SEQ ID NO: 1 is extremely low. Analysis of soluble and insoluble fractions by gel-electrophoresis revealed that only a very small fraction (less than 1%) of the active recombinant protein according to SEQ ID NO: 1 was present in the soluble fraction. The rest of the recombinant protein was present in the inactive form as insoluble inclusion bodies.

We therefore set out to improve the yield of the active, soluble alkaline laccase according to SEQ ID NO: 1 and its analogues.

The present invention is based on our observation that certain single amino acid substitutions in a laccase, preferably an alkaline laccase, improve the yield of that active, soluble laccase when expressed in prokaryotes as well as in eukaryotes. That improvement can be as high as at least 50%, such as at least 100%, 150%, 200%, 400%, 800% or more, such as 1400% or 1700% or more, such as at least 9000%. We also found that the alkaline laccase retains its specific activity (activity per weight of the enzyme).

The term "laccase" as used herein refers to a polypeptide with laccase activity (EC 1.10.3.2). The term "alkaline laccase" refers to a laccase with an optimal activity above pH of 7.0.

The term "laccase activity" is used herein to mean the property of a polypeptide to act as a laccase enzyme, which may be expressed as the maximal initial rate of the specific oxidation reaction. Laccase activity may be determined by standard oxidation assays known in the art including, such as for example by measurement of oxidation of DMP (2,6-Dimethoxyphenol), according to Koschorreck et al 2008 [7].

As used herein, the term "specific activity" refers to the activity per weight of an enzyme. Increased or improved specific activity of a mutated or variant laccase refers to a laccase activity higher than that of a corresponding non-mutated laccase enzyme under the same conditions for the same amount, expressed as weight of laccase protein.

As used herein, the term "Volumetric activity" refers to the activity per volume unit of the production culture. Increased or improved volumetric activity of a mutated or variant laccase refers to a laccase activity higher than that of a corresponding non-mutated laccase enzyme obtained from the same production culture volume.

As used herein, the term "Relative activity" (expressed in %) refers to the fraction of laccase activity per volume of an enzyme (volumetric activity) as compared to the control enzyme, whereas the activity of the control enzyme in the same volume is taken as 100%.

The term "amino acid substitution" or "amino acid substitutions" is used herein in the same way as it is commonly used, i.e. the term refers to a replacement of one or more amino acids in a protein, at a certain position, with another amino acid. Such amino acid substitutions may also be referred to as "variants" or "mutations".

The term "amino acid variant", "laccase variant" or "sequence variant" or "mutant" or equivalent has a meaning well recognized in the art and is accordingly used herein to indicate an amino acid sequence that differs from another amino acid sequence by at least one amino acid.

SEQ ID NO: 1 represents the amino acid sequence of a CotA laccase from *Bacillus wacoensis* that has been previously disclosed and has Accession number WP_034742460.1 in the Protein database of the National Center of Biotechnology Information at the US National Library of Medicine at National institute of Health (https://www.ncbi.nlm.nih.gov/protein/).

We found that certain variants of this laccase provided a higher yield of active laccase when expressed in a heterologous expression system, such as *E. coli*.

The term "higher yield", "increased yield" or "improved yield" or equivalent means that the yield of active enzyme from the same culture volume obtained in a standard purification or recovery protocol is increased, preferably by at least 50% or a factor 1.5. The increase may be even more, such as a factor 2, 2.5, 3, 4, 5, 6, 7, 8, 9 10, 11, 12, 13, 14, 15 or more. An example of determining relative laccase activity is presented in Example 4. Any substrate suitable for the enzyme in question may be used in the activity measurements. A non-limiting example of a substrate suitable for use in assessing the enzymatic activity of laccase variants is DMP (2,6-Dimethoxyphenol). Laccases are able to oxidise this substrate.

Recovery of a laccase variant produced by a host cell may be performed by any technique known to those skilled in the art. Possible techniques include, but are not limited to secretion of the protein into the expression medium, and purification of the protein from cellular biomass. The production method may further comprise a step of purifying the laccase variant obtained. For thermostable laccases, non-limiting examples of such methods include heating of the disintegrated cells and optionally removing coagulated thermo labile proteins from the solution. For secreted proteins, non-limiting examples of such methods include ion exchange chromatography, and ultra-filtration of the expression medium. It is important that the purification method of choice is such that the purified protein retains its activity, preferably its laccase activity.

Accordingly, in one embodiment, the invention relates to a variant of a parent polypeptide wherein the parent polypeptide comprises an amino acid sequence according to SEQ ID NO: 1 and wherein the variant polypeptide has laccase activity (EC 1.10.3.2), and wherein the variant polypeptide comprises at least one amino acid selected from the group consisting of:

Alanine at a position corresponding to position 253 in SEQ ID NO: 1,
Proline at a position corresponding to position 128 in SEQ ID NO: 1,
Aspartic acid at a position corresponding to position 384 in SEQ ID NO: 1,
Isoleucine at a position corresponding to position 364 in SEQ ID NO: 1,
Proline at a position corresponding to position 292 in SEQ ID NO: 1,
Proline at a position corresponding to position 450 in SEQ ID NO: 1,
Threonine at a position corresponding to position 33 in SEQ ID NO: 1 and
Proline at a position corresponding to position 322 in SEQ ID NO: 1.

We found that these variant polypeptides were obtained in a higher yield as compared to the yield of the polypeptide according to SEQ ID NO: 1, when expressed in a recombinant expression system such as *E. coli*. Table 1 provides the activity of the individual variant polypeptides relative to the activity of the wild type *B. wakoensis* laccase according to SEQ ID NO: 1.

TABLE 1

Relative expression levels of individual variants.

| SEQ ID NO: | Variant Amino Acid | Relative activity (%) |
|---|---|---|
| 1 | Wild type *B. wakoensis* laccase | 100 |
| 2 | G253A | 1700 |
| 3 | S128P | 200 |
| 4 | N384D | 500 |
| 5 | H364I | 210 |
| 6 | S292P | 360 |
| 7 | A450P | 220 |

TABLE 1-continued

Relative expression levels of individual variants.

| SEQ ID NO: | Variant Amino Acid | Relative activity (%) |
|---|---|---|
| 8 | Q33T | 200 |
| 9 | A322P | 260 |

The individual variants are herein referred to as follows. When referring to substitutions in a polypeptide according to SEQ ID NO: 1: G253A refers to a substitution of Glycine at position 253 in SEQ ID NO: 1 with an Alanine (SEQ ID NO: 2), S128P refers to a substitution of Serine at position 128 in SEQ ID NO: 1 with a Proline (SEQ ID NO: 3), N384D refers to a substitution of Asparagine at position 384 in SEQ ID NO: 1 with an Aspartic Acid (SEQ ID NO: 4), H364I refers to a substitution of Histidine at position 364 in SEQ ID NO: 1 with an Isoleucine (SEQ ID NO: 5), S292P refers to a substitution of Serine at position 292 in SEQ ID NO: 1 with a Proline (SEQ ID NO: 6), A450P refers to a substitution of Alanine at position 450 in SEQ ID NO: 1 with a Proline (SEQ ID NO: 7), Q33T refers to a substitution of Glutamine at position 33 in SEQ ID NO: 1 with a Threonine (SEQ ID NO: 8) and A322P refers to a substitution of Alanine at position 322 in SEQ ID NO: 1 with a proline (SEQ ID NO: 9).

In the Examples sections it is detailed how these variants were prepared each individually, and in combinations. It appeared that the effect of the combinations of the individual substitutions was additive. This means that, when two variations were introduced into a single variant polypeptide, the yield of that "double mutant" polypeptide was higher as compared to the yield of a polypeptide with each of the two amino acid substitutions separately. This is detailed in Table 2 which shows the effect on yield of all possible combinations of two different variant amino acids into a single variant polypeptide.

TABLE 2

Effect of two individual amino acid substitutions into a single variant polypeptide.

| SEQ ID NO: | Variant Amino Acids | Relative activity (%) |
|---|---|---|
| 1 | Wild type *B. wakoensis* laccase | 100 |
| 10 | G253A + S128P | 3400 |
| 11 | G253A + N384D | 8500 |
| 12 | G253A + H364I | 3570 |
| 13 | G253A + S292P | 6120 |
| 14 | G253A + A450P | 3740 |
| 15 | G253A + Q33T | 3400 |
| 16 | G253A + A322P | 4420 |
| 17 | S128P + N384D | 1000 |
| 18 | S128P + H364I | 420 |
| 19 | S128P + S292P | 720 |
| 20 | S128P + A450P | 440 |
| 21 | S128P + Q33T | 400 |
| 22 | S128P + A322P | 520 |
| 23 | N384D + H364I | 1050 |
| 24 | N384D + S292P | 1800 |
| 25 | N384D + A450P | 1100 |
| 26 | N384D + Q33T | 1000 |
| 27 | N384D + A322P | 1300 |
| 28 | H364I + S292P | 756 |
| 29 | H364I + A450P | 462 |
| 30 | H364I + Q33T | 420 |
| 31 | H364I + A322P | 546 |
| 32 | S292P + A450P | 792 |
| 33 | S292P + Q33T | 720 |
| 34 | S292P + A322P | 936 |
| 35 | A450P + Q33T | 440 |

TABLE 2-continued

Effect of two individual amino acid substitutions into a single variant polypeptide.

| SEQ ID NO: | Variant Amino Acids | Relative activity (%) |
|---|---|---|
| 36 | A450P + A322P | 572 |
| 37 | Q33T + A322P | 520 |

It further appeared that the effect of the combinations of individual substitutions was also additive when more than two variant amino acids were combined into a single variant polypeptide. Also in this case, the yield of that polypeptide was higher as compared to the yield of a polypeptide with any of the variant amino acid substitutions separately. This is detailed in Table 3 which shows the effect on yield of several combinations selected from eight different variant amino acids into a single variant polypeptide.

It appeared that each individual variant amino acid added an additional effect on the yield of the variant polypeptide (table 3).

TABLE 3 relative expression levels of combined variants

| SEQ ID NO: | Variant | Relative activity (%) |
|---|---|---|
| 1 | Wild type B. wakoensis laccase | 100 |
| 2 | G253A | 1700 |
| 10 | G253A + S128P | 3400 |
| 38 | G253A+ S128P + N384D | 6144 |
| 39 | G253A + S128P + N384D + H364I | 6758 |
| 40 | G253A + S128P + N384D + H364I + S292P | 8110 |
| 41 | G253A + S128P + N384D + H364I + S292P + A450P | 8515 |
| 42 | G253A + S128P + N384D + H364I + S292P + A450P + Q33T | 8941 |
| 43 | G253A + S128P + N384D + H364I + S292P + A450P + Q33T +A322P | 9808 |

When expressed in *E. coli*, all variant polypeptides with a single amino acid substitution as described herein showed an increased yield of active soluble enzyme between 200% and 1700% (table 1) as compared to a polypeptide with an amino acid sequence according to SEQ ID NO: 1. In other words, the volumetric activity of the variants was increased to at least 2 times up to 17 times as compared to the wild type sequence of SEQ ID NO: 1.

As a control experiment, we determined whether this improved volumetric activity may be attributable to an increased specific activity of the enzyme. This appeared not to be the case. The increase in the amount of mutated enzymes with an amino acid sequence according to SEQ ID NO: 2-9 in the soluble fraction of *E. coli* cell lysate was approximately proportional to the increase in volumetric activity, so it has to be concluded that more of the active soluble variant enzyme had been recovered. It appeared therefore that the increase in activity was attributable to the increase in the amount of soluble protein rather that an increase of the specific activity.

We determined the total amount of polypeptide (soluble plus unsoluble) in a quantitative SDS PAGE electrophoresis. It appeared that the total amount of polypeptide produced in a given prokaryotic host was constant, whereas the soluble fraction increased and the insoluble fraction decreased. This in turn contributes to an increase of active, correctly folded variant polypeptides.

Identical results were obtained when the wild-type polypeptide and its variants according to SEQ ID NO:s 2-9 were expressed in *Bacillus subtilis*. Therewith it has become clear that the increase in relative activity of the variant polypeptides as produced in prokaryotic expression systems is an inherent property of the polypeptide itself, rather than an increase of the efficiency of the production of it. It is also clear therewith that the inherent property of a better foldability of the mutant polypeptides is independent of the expression system, whether expressed in a Eukaryotic or Prokaryotic system, the mutant polypeptides were inherently more active.

Without wishing to be bound by theory, we anticipate that the mutations as disclosed above, contribute to a better folding of the polypeptide, thereby increasing the relative amount of soluble polypeptide, hence the increase in relative volumetric activity. Or, in other words, the relative fraction of insoluble, misfolded and inactive polypeptides is larger in the wild-type polypeptides produced in prokaryotes, as compared to the fraction of correctly folded, active, variant polypeptides.

In Eukaryotic expression systems, the misfolded polypeptides do not form inclusion bodies, but are rather immediately directed into the proteolysis system. Therefore an increase in the solubility of a variant polypeptide can only be measured as an increase in the amount of active protein. Inactive protein which is misfolded is immediately directed to the proteolytic system and cannot be measured in the fraction of total polypeptide produced.

In accordance with the above observation that the polypeptides carrying the herein described mutation or mutations are more soluble and less prone to mis-folding, we observed an increase of soluble polypeptide of the variant polypeptides when expressed in a Eukaryotic expression system.

When the variants according to SEQ ID NO: 2-9 were expressed in *Pichia pastoris*, the eukaryotic expression also showed an increased yield for all variants (table 4). The protein yield was increased to at least 150% as compared to the wild type (SEQ ID NO: 1). This again supports the notion that the variant polypeptides are more soluble and better folded than the wild-type polypeptide. Less protein is directed to the proteolytic system which translates in an increase of total (soluble) protein.

TABLE 4

Relative expression levels of individual variants in *Pichia pastoris*.

| SEQ ID NO: | Variant Amino Acid | Relative activity (%) |
|---|---|---|
| 1 | Wild type B. wakoensis laccase | 100 |
| 2 | G253A | 1450 |
| 3 | S128P | 160 |
| 4 | N384D | 350 |
| 5 | H364I | 180 |
| 6 | S292P | 280 |
| 7 | A450P | 180 |
| 8 | Q33T | 150 |
| 9 | A322P | 200 |

The teaching as provided herein should not be so narrowly construed as that it relates only to the exemplified sequence of SEQ ID NO: 1 and its variant polypeptides. It is well known in the art that protein sequences may be altered or optimized, for instance by site-directed mutagenesis, in order to arrive at related proteins with identical or even improved properties.

We performed a homology search for proteins homologous to SEQ ID NO: 1 using SEQ ID NO: 1 as the query sequence in the "Standard protein BLAST" software, available at http://blast.ncbi.nlm.nih.gov/Blast.cgi?PROGRAM=blastp&PAGE_TYPE=BlastSearch&LINK_LOC=blasthome. More information on the software and database versions is available at the National Center for Biotechnology Information at National Library of Medicine at National Institute of Health internet site www.ncbi.nlm.nih.gov. Therein, a number of molecular biology tools including BLAST (Basic Logical Alignment Search Tool) is to be found. BLAST makes use of the following databases: All non-redundant GenBank CDS translations+PDB+SwissProt+PIR+PRF excluding environmental samples from WGS projects. The search as reported herein was performed online on 16 Jan. 2018 and employed BLAST+ version 2.6.0 (web-based).

The search revealed that the closest homologue of SEQ ID NO: 1 has 72% identity to SEQ ID NO: 1. This sequence was from a copper oxidase from *Bacillus salsus*, accession number WP_090849688.1 (SEQ ID NO: 44). So it may be concluded that there are no laccases known to exist in nature or anywhere else with an amino acid sequence that is more than 75% identical to the laccase according to SEQ ID NO: 1. Nevertheless, such proteins may now be artificially constructed and expressed in a recombinant expression system. It is well within reach of the skilled person to construct such closely related proteins with a sequence identity of 75% or more, such as 80%, 85%, 90% or more and test them for laccase or alkaline laccase activity.

Introduction of a specific variation in a recombinant gene is among the routine skills of a molecular biologist. Comprehensive guidance may be obtained from Methods in Molecular Biology Vol 182, "In vitro mutagenesis protocols", Eds Jeff Braman, Humana Press 2002. There are commercially available kits for performing site-directed mutagenesis (for example, QuikChange II XL Site-Directed Mutagenesis kit Agilent Technologies cat No 200521).

Hence, the invention relates to a variant polypeptides having laccase activity, homologues thereof and methods for their use and production as described herein, wherein the variant polypeptide comprises or consists of an amino acid sequence at least 90% identical to SEQ ID NO: 1. The term "at least 90%", is to be interpreted as 90%, 91, 92, 93, 94, 95, 96, 97, 98, 99% or more.

More specifically, the invention relates to a polypeptide with laccase activity (EC 1.10.3.2) comprising an amino acid sequence that is at least 90% identical to the amino acid sequence according to SEQ ID NO: 1, wherein the polypeptide comprises at least one amino acid selected from the group consisting of:

Alanine at a position corresponding to position 253 in SEQ ID NO: 1,
Proline at a position corresponding to position 128 in SEQ ID NO: 1,
Aspartic acid at a position corresponding to position 384 in SEQ ID NO: 1,
Isoleucine at a position corresponding to position 364 in SEQ ID NO: 1,
Proline at a position corresponding to position 292 in SEQ ID NO: 1,
Proline at a position corresponding to position 450 in SEQ ID NO: 1,
Threonine at a position corresponding to position 33 in SEQ ID NO: 1 and
Proline at a position corresponding to position 322 in SEQ ID NO: 1.

The laccases as presented herein share the technical feature that they have an improved yield when expressed in a recombinant host cell such as *E. coli*, as compared to the yield of a polypeptide according to SEQ ID NO: 1.

The phrase "amino acid at a position corresponding to position xxx", as used herein, wherein xxx is a number, is to be interpreted as follows. In order to determine whether an amino acid at a certain position in a first amino acid sequence corresponds to a certain amino acid in a second amino acid sequence, the first and second amino acid sequences first have to be aligned using standard software available in the art, such as the "Align" tool at NCBI recourse http://blast.ncbi.nlm.nih.gov/Blast.cgi?PAGE_TYPE=BlastSearch&BLAST_SPEC=blast2seq&LINK_LOC=align2seq The corresponding amino acid positions then follow from that alignment. So for example, if the first amino acid sequence consists of 13 amino acids, and the second amino acid sequence is identical, except for a deletion of amino acids 5 and 6, then an alignment of these sequences would look like:

```
1 MRRKLEKFVDSLP 13 (SEQ ID NO: 63)
  ||||  |||||||
1 MRRK--KFVDSLP 11 (SEQ ID NO: 64)
```

Then amino acid D at position 8 of the second amino acid sequence (SEQ ID NO: 64) is said to be at a position that corresponds with position 10 of the first amino acid sequence (SEQ ID NO: 63). Further examples of alignment of sequences and guidance in the process of finding corresponding positions are to be found in the examples section.

In different terms, the invention relates to a variant of a parent enzyme having laccase activity (EC 1.10.3.2), which variant has an improved yield when expressed in a recombinant expression system such as *E. coli*, compared to said parent enzyme, and which variant comprises at least one mutation selected from the group consisting of:

Alanine at a position corresponding to position 253 in SEQ ID NO: 1,
Proline at a position corresponding to position 128 in SEQ ID NO: 1,
Aspartic acid at a position corresponding to position 384 in SEQ ID NO: 1,
Isoleucine at a position corresponding to position 364 in SEQ ID NO: 1,
Proline at a position corresponding to position 292 in SEQ ID NO: 1,
Proline at a position corresponding to position 450 in SEQ ID NO: 1,
Threonine at a position corresponding to position 33 in SEQ ID NO: 1 and
Proline at a position corresponding to position 322 in SEQ ID NO: 1, wherein the parent enzyme is a laccase comprising an amino acid sequence according to SEQ ID NO: 1 or a laccase comprising an amino acid sequence that is at least 90% identical to SEQ ID NO: 1.

The laccase variants according to the present invention may be used in a wide range of different industrial processes and applications, such as lignin oxidation, polymerisation or depolymerisation, cellulose recovery from lignocellulosic biomass, decreasing refining energy in wood refining and pulp preparation, in pulp delignification, textile dye bleaching, wastewater detoxification, xenobiotic detoxification, and detergent manufacturing.

Amino acid variations as described herein may be introduced into any of the amino acid sequences disclosed herein, or other homologous sequences, by standard methods known in the art, such as site-directed mutagenesis. In this way, the yield of the laccases from a heterologous expression system may be improved.

Kits for performing site-directed mutagenesis are commercially available in the art (e.g. QuikChange® II XL Site-Directed Mutagenesis kit by Agilent Technologies). Further suitable methods for introducing the above mutations into a recombinant gene are disclosed e.g. in Methods in Molecular Biology, 2002 [8].

Thus, in some embodiments, the present invention relates to laccase variants or mutants which comprise at least one of the variant amino acids selected from the group consisting of 253A, 128P, 384D, 364I, 292P, 450P, 33T and 322P, as listed above.

In respect to a laccase polypeptide according to the invention; the abbreviation 253A refers to an Alanine residue at a position corresponding to position 253 in SEQ ID NO: 1, 128P refers to a Proline residue at a position corresponding to position 128 in SEQ ID NO: 1, 384D refers to an Aspartic acid at a position corresponding to position 384 in SEQ ID NO: 1, 364I refers to an Isoleucine residue at a position corresponding to position 364 in SEQ ID NO: 1, 292P refers to a Proline residue at a position corresponding to position 292 in SEQ ID NO: 1, 450P refers to a Proline residue at a position corresponding to position 450 in SEQ ID NO: 1, 33T refers to a Threonine residue at a position corresponding to position 33 in SEQ ID NO: 1 and 322P refers to a Proline residue at a position corresponding to position 322 in SEQ ID NO: 1.

The term "heterologous expression system" or "recombinant expression system" or equivalent means a system for expressing a DNA sequence from one host organism in a recipient organism from a different species or genus than the host organism. The most prevalent recipients, known as heterologous expression systems, are chosen usually because they are easy to transfer DNA into or because they allow for a simpler assessment of the protein's function. Heterologous expression systems are also preferably used because they allow the upscaling of the production of a protein encoded by the DNA sequence in an industrial process. Preferred recipient organisms for use as heterologous expression systems include bacterial, fungal and yeast organisms, such as for example *Escherichia coli, Bacillus, Corynebacterium, Pseudomonas, Pichia pastoris, Saccharomyces cerevisiae, Yarrowia lipolytica*, filamentus fungi and many more systems well known in the art.

As used herein, the degree of identity between two or more amino acid sequences is equivalent to a function of the number of identical positions shared by the sequences (i.e., % identity=number of identical positions divided by the total number of positions×100), excluding gaps, which need to be introduced for optimal alignment of the two sequences, and overhangs. The comparison of sequences and determination of percent identity between two or more sequences can be accomplished using standard methods known in the art. For example, a freeware conventionally used for this purpose is "Align" tool at NCBI recourse http://blast.ncbi.nlm.nih.gov/Blast.cgi?PAGE_TYPE=BlastSearch&BLAST_SPEC=blast2seq&LINK_LOC=align2seq In a preferred embodiment the alignment of two sequences is to be performed over the full length of the polypeptides.

The variant laccase polypeptides or proteins as disclosed herein may be fused to additional sequences, such as for instance by attaching or inserting sequences encoding affinity tags, thereby facilitating protein purification (S-tag, maltose binding domain, chitin binding domain). Domains or sequences assisting folding (such as thioredoxin domain, SUMO protein), sequences affecting protein localization (periplasmic localization signals etc), proteins bearing additional function, such as green fluorescent protein (GFP), or sequences representing another enzymatic activity may also be attached. Other suitable fusion partners for the present laccases are known to those skilled in the art.

The present invention also relates to polynucleotides encoding any of the laccase variants disclosed herein. Means and methods for cloning and isolating such polynucleotides are well known in the art.

Furthermore, the present invention relates to a vector comprising a polynucleotide according to the invention, optionally operably linked to one or more control sequences. Suitable control sequences are readily available in the art and include, but are not limited to, promoter, leader, polyadenylation, and signal sequences.

Laccase variants according to various embodiments of the present invention may be obtained by standard recombinant methods known in the art. Briefly, such a method may comprise the steps of i) culturing a desired recombinant host cell under conditions suitable for the production of a present laccase polypeptide variant, and ii) recovering the polypeptide variant obtained. The polypeptide may then optionally be further purified.

A large number of vector-host systems known in the art may be used for recombinant production of laccase variants. Possible vectors include, but are not limited to, plasmids or modified viruses which are maintained in the host cell as autonomous DNA molecule or integrated in genomic DNA. The vector system must be compatible with the host cell used as is well known in the art. Non-limiting examples of suitable host cells include bacteria (e.g. *E. coli*, bacilli), yeast (e.g. *Pichia Pastoris, Saccharomyces Cerevisae*), fungi (e.g. filamentous fungi) insect cells (e.g. Sf9).

In yet other terms, the invention relates to a method for improving the yield of a polypeptide with laccase activity in a heterologous expression system comprising the step of altering at least one amino acid at a position selected from the group consisting of positions corresponding to positions 253, 128, 384, 364, 292, 450, 33 and 322 in SEQ ID NO: 1 into an Alanine, Proline, Aspartic acid, Isoleucine, Proline, Proline, Threonine and Proline respectively, wherein the polypeptide with laccase activity is a polypeptide with an amino acid sequence according to SEQ ID NO: 1 or a polypeptide with an amino acid sequence that is at least 90% identical to the sequence of SEQ ID NO: 1.

In a preferred embodiment of the invention, the above method comprises a step of altering 2, 3, 4, 5, 6, 7 or 8 amino acids selected from the group of amino acids present at positions corresponding to positions 253, 128, 384, 364, 292, 450, 33 and 322 in SEQ ID NO: 1.

TABLE 5

Sequences as disclosed herein

| SEQ ID NO: | Mutation(s)/Name | Sequence |
|---|---|---|
| 1 | Wild type B. wakoensis laccase | MRRKLEKFVDSLPIMETLQPKTKGKNYYEVKIQEFKKKLLHRDLPPTTLWGYNAQPPGPTIEANSNEPVEVKWINELPNKHFLPVDWSIMN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 2 | G253A | MRRKLEKFVDSLPIMETLQPKTKGKNYYEVKIQEFKKKLLHRDLPPTTLWGYNAQPPGPTIEANSNEPVEVKWINELPNKHFLPVDWSIMN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNASNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 3 | S128P | MRRKLEKFVDSLPIMETLQPKTKGKNYYEVKIQEFKKKLLHRDLPPTTLWGYNAQPPGPTIEANSNEPVEVKWINELPNKHFLPVDWSIMN KDLPEVRHVTHLHGGRTPWVSDGYPEAWTKDYKEVGPFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 4 | N384D | MRRKLEKFVDSLPIMETLQPKTKGKNYYEVKIQEFKKKLLHRDLPPTTLWGYNAQPPGPTIEANSNEPVEVKWINELPNKHFLPVDWSIMN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLDNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 5 | H364I | MRRKLEKFVDSLPIMETLQPKTKGKNYYEVKIQEFKKKLLHRDLPPTTLWGYNAQPPGPTIEANSNEPVEVKWINELPNKHFLPVDWSIMN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTIRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 6 | S292P | MRRKLEKFVDSLPIMETLQPKTKGKNYYEVKIQEFKKKLLHRDLPPTTLWGYNAQPPGPTIEANSNEPVEVKWINELPNKHFLPVDWSIMN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIEPSERIDVIIDFSQCDGDEIVLKNDLGPDADAEDETNEIMKFKVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |

TABLE 5 -continued

Sequences as disclosed herein

| SEQ ID NO: | Mutation(s)/Name | Sequence |
|---|---|---|
| 7 | A450P | MRRKLEKFVDSLPIMETLQPKTKGKNYYEVKIQEFKKKLHRDLPTTLWGYNAQFPGPTIEANSNEPVEVKWINELPNKHFLPVDWSIMN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRP PEPNERGWKDTVSAPAGQITRVIGTFAPYTGNYVWHCHILEHEDHDMMRPMKVIDPKQRKDK |
| 8 | Q33T | MRRKLEKFVDSLPIMETLQPKTKGKNYYEVKITEFKKKLHRDLPTTLWGYNAQFPGPTIEANSNEPVEVKWINELPNKHFLPVDWSINN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 9 | A322P | MRRKLEKFVDSLPIMETLQPKTKGKNYYEVKIQEFKKKLHRDLPTTLWGYNAQFPGPTIEANSNEPVEVKWINELPNKHFLPVDWSINN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIESSERIDVIIDFSQCDGDEIVLKNDLGPDADPEDETNEIMKFKVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 10 | G253A + S128P | MRRKLEKFVDSLPIMETLQPKTKGKNYYEVKIQEFKKKLHRDLPTTLWGYNAQFPGPTIEANSNEPVEVKWINELPNKHFLPVDWSINN KDLPEVRHVTHLHGGRTPWVSDGYPEAWTKDYKEVGPFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNASNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 11 | G253A + N384D | MRRKLEKFVDSLPIMETLQPKTKGKNYYEVKIQEFKKKLHRDLPTTLWGYNAQFPGPTIEANSNEPVEVKWINELPNKHFLPVDWSINN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNASNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLDNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 12 | G253A + H364I | MRRKLEKFVDSLPIMETLQPKTKGKNYYEVKIQEFKKKLHRDLPTTLWGYNAQFPGPTIEANSNEPVEVKWINELPNKHFLPVDWSINN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNASNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTIRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 13 | G253A + S292P | MRRKLEKFVDSLPIMETLQPKTKGKNYYEVKIQEFKKKLHRDLPTTLWGYNAQFPGPTIEANSNEPVEVKWINELPNKHFLPVDWSINN KDLPEVRHVTHLHGGRTPWVSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNASNTRSYQLHLDSNQEVY QIGSDGGLLEKPVQMNKIPIEPSERIDVIIDFSQCDGDEIVLKNDLGPDADAEDETNEIMKFKVSKPLKEKDTSVIPKRLSTIRSLRNNK |

TABLE 5 -continued

Sequences as disclosed herein

| SEQ ID NO: | Mutation(s)/ Name | Sequence |
|---|---|---|
| | | ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 14 | G253A + A450P | MRRKLEKFVDSLPIMETLQPKTKGKNYYEVKIQEFKKKLHRDLPTTLWGYNAQPPGPTIEANSNEPVEVKWINELPNKHFLPVDWSIMN KDLPEVRHVTHLHGGRTPWVSDGYPEAWYTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNASNTRSYQLHLDSNQEVY QIGSDGGLLEKPVQMNKIPIESSERIDVIIDFSQCDGDEIVLKNDLGPDADAEDETNEIMKFVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRP PEPNERGWKDTVSAPAGQITRVIGTFAPYTGNYVWHCHILEHEDHDMMRPMKVIDPKQRKDK |
| 15 | G253A + Q33T | MRRKLEKFVDSLPIMETLQPKTKGKNYYEVKITEFKKKLHRDLPTTLWGYNAQPPGPTIEANSNEPVEVKWINELPNKHFLPVDWSIMN KDLPEVRHVTHLHGGRTPWVSDGYPEAWYTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNASNTRSYQLHLDSNQEVY QIGSDGGLLEKPVQMNKIPIESSERIDVIIDFSQCDGDEIVLKNDLGPDADAEDETNEIMKFVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 16 | G253A + A322P | MRRKLEKFVDSLPIMETLQPKTKGKNYYEVKIQEFKKKLHRDLPTTLWGYNAQPPGPTIEANSNEPVEVKWINELPNKHFLPVDWSIMN KDLPEVRHVTHLHGGRTPWVSDGYPEAWYTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNASNTRSYQLHLDSNQEVY QIGSDGGLLEKPVQMNKIPIESSERIDVIIDFSQCDGDEIVLKNDLGPDADPEDETNEIMKFVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 17 | S128P + N384D | MRRKLEKFVDSLPIMETLQPKTKGKNYYEVKIQEFKKKLHRDLPTTLWGYNAQPPGPTIEANSNEPVEVKWINELPNKHFLPVDWSIMN KDLPEVRHVTHLHGGRTPWVSDGYPEAWYTKDYKEVGPFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFVSKPLKEKDTSVIPKRLSTIRSLRNNK ISTIRNLKLVGSTDDFGRPLLLDNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 18 | S128P+ H364I | MRRKLEKFVDSLPIMETLQPKTKGKNYYEVKIQEFKKKLHRDLPTTLWGYNAQPPGPTIEANSNEPVEVKWINELPNKHFLPVDWSIMN KDLPEVRHVTHLHGGRTPWVSDGYPEAWYTKDYKEVGPFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 19 | S128P + S292P | MRRKLEKFVDSLPIMETLQPKTKGKNYYEVKIQEFKKKLHRDLPTTLWGYNAQPPGPTIEANSNEPVEVKWINELPNKHFLPVDWSIMN KDLPEVRHVTHLHGGRTPWVSDGYPEAWYTKDYKEVGPFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIEPSERIDVIIDFSQCDGDEIVLKNDLGPDADAEDETNEIMKFVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 20 | S128P + A450P | MRRKLEKFVDSLPIMETLQPKTKGKNYYEVKIQEFKKKLHRDLPTTLWGYNAQPPGPTIEANSNEPVEVKWINELPNKHFLPVDWSIMN KDLPEVRHVTHLHGGRTPWVSDGYPEAWYTKDYKEVGPFFKEEVYRYLNEQRAMMLWYHDHTMGITRLNNYAGLAGAYIIRDKHEKSLNL |

TABLE 5-continued

Sequences as disclosed herein

| SEQ ID NO: | Mutation(s)/Name | Sequence |
|---|---|---|
| 21 | S128P + Q33T | MRRKLEKFVDSLPIMETLQPKTKGKNYYEVKITEPKKKLHRDLPPTTLWGYNAQPFGPTIEANSNEPVEVKWINELPNKHFLPVDWSIMN KDLPEVRHVTHLHGGRTPWSDGYPEAWTKDYKEVGPFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLLNNKKWADPTTEKPKVGDTEWVSFINTTDFAHPMHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 22 | S128P + A322P | MRRKLEKFVDSLPIMETLQPKTKGKNYYEVKIQEFKKKLHRDLPPTTLWGYNAQPFGPTIEANSNEPVEVKWINELPNKHFLPVDWSIMN KDLPEVRHVTHLHGGRTPWSDGYPEAWTKDYKEVGPFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADPEDETNEIMKFKVSKPLKEKDTSVIPKRLSTIRSLRNNK ISTHRNLKLVGSTDDFGRPLLLLNNKKWADPTTEKPKVGDTEWVSFINTTDFAHPMHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 23 | N384D + H364I | MRRKLEKFVDSLPIMETLQPKTKGKNYYEVKIQEFKKKLHRDLPPTTLWGYNAQPFGPTIEANSNEPVEVKWINELPNKHFLPVDWSIMN KDLPEVRHVTHLHGGRTPWSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTIRNLKLVGSTDDFGRPLLLDNKKWADPTTEKPKVGDTEWVSFINTTDFAHPMHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 24 | N384D + S292P | MRRKLEKFVDSLPIMETLQPKTKGKNYYEVKIQEFKKKLHRDLPPTTLWGYNAQPFGPTIEANSNEPVEVKWINELPNKHFLPVDWSIMN KDLPEVRHVTHLHGGRTPWSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIEPSERIDVIIDFSQCDGDEIVLKNDLGPDADAEDETNEIMKFKVSKPLKEKDTSVIPKRLSTIRSLRNNK ISTHRNLKLVGSTDDFGRPLLLDNKKWADPTTEKPKVGDTEWVSFINTTDFAHPMHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 25 | N384D + A450S | MRRKLEKFVDSLPIMETLQPKTKGKNYYEVKIQEFKKKLHRDLPPTTLWGYNAQPFGPTIEANSNEPVEVKWINELPNKHFLPVDWSIMN KDLPEVRHVTHLHGGRTPWSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLDNKKWADPTTEKPKVGDTEWVSFINTTDFAHPMHLIHFQVLDRQPFDLERYNHDGTIIYTGPPP PEPNERGWKDTVSAPAGQITRVIGTFAPYTGNYVWHCHILEHEDHDMMRPMKVIDPKQRKDK |
| 26 | N384D + Q33T | MRRKLEKFVDSLPIMETLQPKTKGKNYYEVKITEFKKKLHRDLPPTTLWGYNAQPFGPTIEANSNEPVEVKWINELPNKHFLPVDWSIMN KDLPEVRHVTHLHGGRTPWSDGYPEAWTKDYKEVGSFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPDADAEDETNEIMKFKVSKPLKEKDTSVIPKRLSTIRSLRNNK ISTHRNLKLVGSTDDFGRPLLLDNKKWADPTTEKPKVGDTEWVSFINTTDFAHPMHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |

TABLE 5 -continued

Sequences as disclosed herein

| SEQ ID NO: | Mutation(s)/Name | Sequence |
|---|---|---|
| 27 | N384D + A322P | MRRKLEKFVDSLPIMETLQPKTKGNYYEVKIQEFKKKLHRDLPTTLWGYNAQFPGPTIEANSNEPVEVKWINELPNKHFLPVDWSIMN KDLPEVRHVTHLHGGRTPWVSDGYPEAWTKDYKEVGSFFKEEVYRLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIESSERIDVIIDFSQCDGDEIVLKNDLGPDADPEDETNEIMKFVSKPLKEKDTSVIPKRLSTIRSLRNNK ISTHRNLKLVGSTDDFGRPLLLDNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPKVIDPKQRKDK |
| 28 | H364I + S292P | MRRKLEKFVDSLPIMETLQPKTKGNYYEVKIQEFKKKLHRDLPTTLWGYNAQFPGPTIEANSNEPVEVKWINELPNKHFLPVDWSIMN KDLPEVRHVTHLHGGRTPWVSDGYPEAWTKDYKEVGSFFKEEVYRLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIEPSERIDVIIDFSQCDGDEIVLKNDLGPDADAEDETNEIMKFVSKPLKEKDTSVIPKRLSTIRSLRNNK ISTIRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPKVIDPKQRKDK |
| 29 | H364I + A450P | MRRKLEKFVDSLPIMETLQPKTKGNYYEVKIQEFKKKLHRDLPTTLWGYNAQFPGPTIEANSNEPVEVKWINELPNKHFLPVDWSIMN KDLPEVRHVTHLHGGRTPWVSDGYPEAWTKDYKEVGSFFKEEVYRLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIESSERIDVIIDFSQCDGDEIVLKNDLGPDADAEDETNEIMKFVSKPLKEKDTSVIPKRLSTIRSLRNNK ISTIRNLKLVGSTDDFGRPLLLNNKKWADPTTEKPKVGDTEVWSFINTTDFAHPMHIHLIHFQVLDRQPFDLERYNHDGTIIYTGPPPP PEPNERGWKDTVSAPAGQITRVIGTFAPYTGNYVWHCHILEHEDHDMMRPKVIDPKQRKDK |
| 30 | H364I + Q33T | MRRKLEKFVDSLPIMETLQPKTKGNYYEVKITEFKKKLHRDLPTTLWGYNAQFPGPTIEANSNEPVEVKWINELPNKHFLPVDWSIMN KDLPEVRHVTHLHGGRTPWVSDGYPEAWTKDYKEVGSFFKEEVYRLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIESSERIDVIIDFSQCDGDEIVLKNDLGPDADAEDETNEIMKFVSKPLKEKDTSVIPKRLSTIRSLRNNK ISTIRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPKVIDPKQRKDK |
| 31 | H364I + A322P | MRRKLEKFVDSLPIMETLQPKTKGNYYEVKIQEFKKKLHRDLPTTLWGYNAQFPGPTIEANSNEPVEVKWINELPNKHFLPVDWSIMN KDLPEVRHVTHLHGGRTPWVSDGYPEAWTKDYKEVGSFFKEEVYRLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIESSERIDVIIDFSQCDGDEIVLKNDLGPDADPEDETNEIMKFVSKPLKEKDTSVIPKRLSTIRSLRNNK ISTIRNLKLVGSTDDFGRPLLLNNKKWADPTTEKPKVGDTEVWSFINTTDFAHPMHIHLIHFQVLDRQPFDLERYNHDGTIIYTGPPRA PEPNERGWKDTVSAPAGQITRVIGTFAPYTGNYVWHCHILEHEDHDMMRPKVIDPKQRKDK |
| 32 | S292P + A450P | MRRKLEKFVDSLPIMETLQPKTKGNYYEVKIQEFKKKLHRDLPTTLWGYNAQFPGPTIEANSNEPVEVKWINELPNKHFLPVDWSIMN KDLPEVRHVTHLHGGRTPWVSDGYPEAWTKDYKEVGSFFKEEVYRLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIEPSERIDVIIDFSQCDGDEIVLKNDLGPDADAEDETNEIMKFVSKPLKEKDTSVIPKRLSTIRSLRNNK ISTHRNLKLVGSTDDFGRPLLLNNKKWADPTTEKPKVGDTEVWSFINTTDFAHPMHIHLIHFQVLDRQPFDLERYNHDGTIIYTGPPPP PEPNERGWKDTVSAPAGQITRVIGTFAPYTGNYVWHCHILEHEDHDMMRPKVIDPKQRKDK |
| 33 | S292P + Q33T | MRRKLEKFVDSLPIMETLQPKTKGNYYEVKITEFKKKLHRDLPTTLWGYNAQFPGPTIEANSNEPVEVKWINELPNKHFLPVDWSIMN KDLPEVRHVTHLHGGRTPWVSDGYPEAWTKDYKEVGSFFKEEVYRLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFILNGSNTRSYQLHLDSNQEVY QIGSDGGLLEKPVQMNKIPIEPSERIDVIIDFSQCDGDEIVLKNDLGPDADAEDETNEIMKFVSKPLKEKDTSVIPKRLSTIRSLRNNK |

| SEQ ID NO: | Mutation(s)/Name | Sequence |
|---|---|---|
| | | ISTHRNLKLVGSTDDFGRPLLLLNNKKWADPTTEKPKVGDTEWMINTTDFAHPMIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 34 | S292P + A322P | MRRKLEKFVDSLPIMETLQPKTKGKNYYEVKIQEFKKKLHRDLPPTTLWGYNAQPPGPTIEANSNEPVEVKWINELPNKHFLPVDWSIMN KDLPEVRHVTHLHGGRTPWVSDGYPEAWYTKDYKEVGSFPKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPLEVEPRKYRFRILNGSNTRSYQLHLDSNQEVY QIGSDGGLLEKPVQMNKIPIEPSERIDVIIDFSQCDGDEIVLKNDLGPADPEDETNEIMKFKVSKPLKEKDTSVIPKRLSTIRSLRNNK ISTHRNLKLVGSTDDFGRPLLLLNNKKWADPTTEKPKVGDTEWMINTTDFAHPMIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 35 | A450P + Q33T | MRRKLEKFVDSLPIMETLQPKTKGKNYYEVKITEFKKKLHRDLPPTTLWGYNAQPPGPTIEANSNEPVEVKWINELPNKHFLPVDWSIMN KDLPEVRHVTHLHGGRTPWVSDGYPEAWYTKDYKEVGSFPKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNGSNTRSYQLHLDSNQEVY QIGSDGGLLEKPVQMNKIPIESSERIDVIIDFSQCDGDEIVLKNDLGPADPEDETNEIMKFKVSKPLKEKDTSVIPKRLSTIRSLRNNK ISTHRNLKLVGSTDDFGRPLLLLNNKKWADPTTEKPKVGDTEWMINTTDFAHPMIHLIHFQVLDRQPFDLERYNHDGTIIYTGPPRP PEPNERGWKDTVSAPAGQITRVIGTFAPYTGNYVWHCHILEHEDHDMMRPMKVIDPKQRKDK |
| 36 | A450P + A322P | MRRKLEKFVDSLPIMETLQPKTKGKNYYEVKIQEFKKKLHRDLPPTTLWGYNAQPPGPTIEANSNEPVEVKWINELPNKHFLPVDWSIMN KDLPEVRHVTHLHGGRTPWVSDGYPEAWYTKDYKEVGSFPKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPLEVEPRKYRFRILNGSNTRSYQLHLDSNQEVY QIGSDGGLLEKPVQMNKIPIESSERIDVIIDFSQCDGDEIVLKNDLGPDADPEDETNEIMKFKVSKPLKEKDTSVIPKRLSTIRSLRNNK ISTHRNLKLVGSTDDFGRPLLLLNNKKWADPTTEKPKVGDTEWMINTTDFAHPMIHLIHFQVLDRQPFDLERYNHDGTIIYTGPPRP PEPNERGWKDTVSAPAGQITRVIGTFAPYTGNYVWHCHILEHEDHDMMRPMKVIDPKQRKDK |
| 37 | Q33T + A322P | MRRKLEKFVDSLPIMETLQPKTKGKNYYEVKITEFKKKLHRDLPPTTLWGYNAQPPGPTIEANSNEPVEVKWINELPNKHFLPVDWSIMN KDLPEVRHVTHLHGGRTPWVSDGYPEAWYTKDYKEVGSFPKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPLEVEPRKYRFRILNGSNTRSYQLHLDSNQEVY QIGSDGGLLEKPVQMNKIPIESSERIDVIIDFSQCDGDEIVLKNDLGPDADPEDETNEIMKFKVSKPLKEKDTSVIPKRLSTIRSLRNNK ISTHRNLKLVGSTDDFGRPLLLLNNKKWADPTTEKPKVGDTEWMINTTDFAHPMIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 38 | G253A + S128P + N384D | MRRKLEKFVDSLPIMETLQPKTKGKNYYEVKIQEFKKKLHRDLPPTTLWGYNAQPPGPTIEANSNEPVEVKWINELPNKHFLPVDWSIMN KDLPEVRHVTHLHGGRTPWVSDGYPEAWYTKDYKEVGPFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNASNTRSYQLHLDSNQEVY QIGSDGGLLEKPVQMNKIPIESSERIDVIIDFSQCDGDEIVLKNDLGPDADEDETNEIMKFKVSKPLKEKDTSVIPKRLSTIRSLRNNK ISTHRNLKLVGSTDDFGRPLLLDNKKWADPTTEKPKVGDTEWMINTTDFAHPMIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 39 | G253A + S128P + N384D + H364I | MRRKLEKFVDSLPIMETLQPKTKGKNYYEVKIQEFKKKLHRDLPPTTLWGYNAQPPGPTIEANSNEPVEVKWINELPNKHFLPVDWSIMN KDLPEVRHVTHLHGGRTPWVSDGYPEAWYTKDYKEVGPFFKEEVYRYLNEQRAMMLWYHDHTMGITRLNNYAGLAGAYIIRDKHEKSLNL PEGEYEVPLIIQDRTFNEDGSLFYPTGPEDGGEDLPNPSIVPAFLGDTVLVNGKVWPYLEVEPRKYRFRILNASNTRSYQLHLDSNQEVY QIGSDGGLLEKPVQMNKIPIESSERIDVIIDFSQCDGDEIVLKNDLGPDAAEDETNEIMKFKVSKPLKEKDTSVIPKRLSTIRSLRNNK ISTIRNLKLVGSTDDFGRPLLLDNKKWADPTTEKPKVGDTEWMINTTDFAHPMIHLIHFQVLDRQPFDLERYNHDGTIIYTGPPRA PEPNERGWKDTVSAPAGQITRVIGTFAPYTGNYVWHCHILEHEDHDMMRPMKVIDPKQRKDK |
| 40 | G253A + S128P + | MRRKLEKFVDSLPIMETLQPKTKGKNYYEVKIQEFKKKLHRDLPPTTLWGYNAQPPGPTIEANSNEPVEVKWINELPNKHFLPVDWSIMN KDLPEVRHVTHLHGGRTPWVSDGYPEAWYTKDYKEVGPFFKEEVYRYLNEQRAMMLWYHDHTMGITRLNNYAGLAGAYIIRDKHEKSLNL |

TABLE 5-continued

Sequences as disclosed herein

| SEQ ID NO: | Mutation(s)/Name | Sequence |
|---|---|---|
| 41 | G253A + S128P + N384D + H364I + S292P + A450P | MRRKLEKFVDSLPIMETLQPKTKGKNYYEVKIQEFKKKLHRDLPPTLWGYNAQFPGPTIEANSNEPVEVKWINELPNKHFLPVDWSIMN KDLPEVRHVTHLHGGRTPWSDGYPEAWYTKDYKEVGPFFKEEVYRYLNEQRAMMLWYHDHTMGITRLNNYAGLAGAYIIRDKHEKSLNL PEGEYEVPLIIQDRTFNEDGSLFYTGPEDGGEDLPNPSIVPAFLGDTVLVNGKVWPYLEVEPRKYRFRILNASNTRSYQLHLDSNQEVY QIGSDGGLLEKPVQMNKIPIEPSERIDVIIDFSQCDGDEIVLKNDLGPDADAEDETNEIMKFKVSKPLKEKDTSVIPKRLSTIRSLRNNK ISTIRNLKLVGSTDDFGRPLLLDNKKWADPTTEKPKVGDTEVWSFINTTDFAHPMIHLIHFQVLDRQPFDLERYNHDGTIIYTGPPRP PEPTERGWKDTVSAPAGQITRVIGTFAPYTGNYVWHCHILEHEDHDMMRPKVIDPKQRKDK |
| 42 | G253A + S128P + N384D + H364I + S292P + A450P + Q33T | MRRKLEKFVDSLPIMETLQPKTKGKNYYEVKITEFKKKLHRDLPPTLWGYNAQFPGPTIEANSNEPVEVKWINELPNKHFLPVDWSIMN KDLPEVRHVTHLHGGRTPWSDGYPEAWYTKDYKEVGPFFKEEVYRYLNEQRAMMLWYHDHTMGITRLNNYAGLAGAYIIRDKHEKSLNL PEGEYEVPLIIQDRTFNEDGSLFYTGPEDGGEDLPNPSIVPAFLGDTVLVNGKVWPYLEVEPRKYRFRILNASNTRSYQLHLDSNQEVY QIGSDGGLLEKPVQMNKIPIEPSERIDVIIDFSQCDGDEIVLKNDLGPDADAEDETNEIMKFKVSKPLKEKDTSVIPKRLSTIRSLRNNK ISTIRNLKLVGSTDDFGRPLLLDNKKWADPTTEKPKVGDTEVWSFINTTDFAHPMIHLIHFQVLDRQPFDLERYNHDGTIIYTGPPRP PEPNERGWKDTVSAPAGQITRVIGTFAPYTGNYVWHCHILEHEDHDMMRPKVIDPKQRKDK |
| 43 | G253A + S128P + N384D + H364I + S292P + A450P + Q33T + A322P | MRRKLEKFVDSLPIMETLQPKTKGKNYYEVKITEFKKKLHRDLPPTLWGYNAQFPGPTIEANSNEPVEVKWINELPNKHFLPVDWSIMN KDLPEVRHVTHLHGGRTPWSDGYPEAWYTKDYKEVGPFFKEEVYRYLNEQRAMMLWYHDHTMGITRLNNYAGLAGAYIIRDKHEKSLNL PEGEYEVPLIIQDRTFNEDGSLFYTGPEDGGEDLPNPSIVPAFLGDTVLVNGKVWPYLEVEPRKYRFRILNASNTRSYQLHLDSNQEVY QIGSDGGLLEKPVQMNKIPIEPSERIDVIIDFSQCDGDEIVLKNDLGPDADPEDETNEIMKFKVSKPLKEKDTSVIPKRLSTIRSLRNNK ISTIRNLKLVGSTDDFGRPLLLDNKKWADPTTEKPKVGDTEVWSFINTTDFAHPMIHLIHFQVLDRQPFDLERYNHDGTIIYTGPPRP PEPTERGWKDTVSAPAGQITRVI7TFAPYTGNYVWHCHILEHEDHDMMRPMKVIDPKQRKDK |
| 44 | Copper oxidase from Bacillus salsus | MSPKLEKFVDQLPIIAALKPNRREADGDYYEITMEEFFQKLHRDLPPTRLWGYNRQVPGPTLDVIQDEPIKVKWNNLPSRHFLPVDKSF LMPDLPEVRTVTHLHGGETPPPSDGYPEAWFTRNYAEVGPFFEREVYEYINQQRATMLWYHDHAMGTTRLNNYAGLAGAYIIRDKYEKSL NLPSGEYEIPLIIQDKSFNRDGSLSYPKQPDNASEDLPNPSVVPAFFGDTILVNGKVWPFLKVEPRKYRFRMLNASNTRGYQLHLDSEQP FYQIGSDGGLLEKPVKLNMITIEPSERMDIILDFSKYEGKDIILRNNLGPNADPENETDEVMKFIVSKPLKEQDKSVIPKRLSTIPSLRA NQISAYRNLKLVGSQDEYGRPLLLLNNKRWADPITEKPRLGTTEIWSFINTTAFAHPMIHLIQFQVLERQPFDLRYNEDGQIIFTGAP |
| 65 | Alkaline laccase from B. clausii | KPPPEPNERGWKDTIKATSGHITRVIGKYGPFTGNYVWHCHILEHEDHDMMRPFKVIE VAHEPEVRTVVHLHGSETTPASDGYPEAWFTKDPAEVGSSFFEQETEYEYPNDQRAATLWTHDHAMGITRLNVYAGLSGLYIIRDPREEQLN LPKGEFDIPLLIQDRSFNDDGSLFYPAQPANPAPNLPNPSVLPFFVGDTILVNGKVWPYLQVEPRKYRFRILNGSNSRSYQLALDSEAPF YQIASDGGLLRRTVSLQAFDIRPAERIEAIIDFSKFEGQTITLKNNASTDATADVMQFQVVLPLSGEDTSIIPQNLSYIPSLQQNDVKRI RNLKISGTTDEYGRPLLLLNNKLWSDPVEEKPCLGTTEIWSFVNVTNVPHPMHILHLVQFQLLDHRAFNVELYNENGQIELVGPTIPPKIN ERGWKDTITAPAGQITRVIARFAPPSGYVWHCHILEHEDYDMRPFVVIDPKTEKERR |

TABLE 5-continued

Sequences as disclosed herein

| SEQ ID NO: | Mutation(s)/ Name | Sequence |
|---|---|---|
| 66 | CotA laccase from B. subtilis | MTLEKFVDALPIPDTLKPVQQTTEKTYYEVTMEECAHQLHRDLPPTRLWGYNGLFPGPTIEVKRNENVVVKWMNNLPSEHFLPIDHTIHH SDSQHEEPEVKTVVHLHGGVTPPDSDGYPEAWFSKDFEQTGPYFKREVVHYPNQQRGATLWYHDHAMALTRLNVYAGLVGAYIIHDPKEK RLKLPSGEYDVPLLITDRTINEDGSLFYPSGPENPSPSLPKPSIVPAFCGDTILVNGKVWPYLEVEPRKYRFRVINASNARTYNLSLDNG GEFIQIGSDGGLLPRSVKLNSFSLAPAERYDIIIDFTAYEGESIILANSEGCGGDANPETDANIMQFRVTKPLAQKDESRKPKYLASYPS VQNERIQNIRTLKLAGTQDEYGRVVQLLNNKRWHDPVTEAPKAGTTEIWSIVNPTQGTHPIHLHLVSFRVLDRRPFDIARYQERGELSYT GPAVPPPSEKGWKDTIQAHAGEVLRIAVTFGPYSGRYVWHCHILEHEDYDMMRPMDITDPHK |
| 67 | CUEO laccase from E. coli | MQRRDFLKYSVALGVASALPLWNRAVFAAERPTLPIPDLLTTDARNRIQLTIGAGQSTFGGKTATTWGYNGNLLGPAVKLQRGKAVTVDI YNQLTEETTLHWHGLEVPGEVDGGPQGIIPPGGKRSVTLNVDQPAATCWFHPHQHGKTGRQVAMGLAGLVVIEDDEILKLMLPKQWGIDD VPVIVQDKKFSADGQIDYQLDVMTAAVGWFGDTLLTNGAIYPQHAAPRGWLRLLNGCNARSLNFATSDNRPLYVIASDGGLLPEPVKV SELPVLMGERFEVLVEVNDNKPFDLVTLPVSQMGMAIAPDKPHPVMRIQPIAISASGALPDTLSSLPALPSLEGLTVRKLQLSMDPMLD MMGMQMLMEKYGDQAMAGNMDHSQMMGHMGHGNMNHMNHGGKFDFHHANKINGQAFDMNKPMFAAAKGQYERWVISGVGDMMLHPFHIHGT QFRILSENGKPPAAHRAGWKDTVKVEGNVSEVLVKFNHDAPKEHAYMAHCHLLEHEDTGMMLGFTVSDP |

Examples

Example 1: Construction of Laccases with Improved Properties

Mutations as described herein were introduced into various recombinant genes by standard site-directed mutagenesis essentially as described in WO 2013/038062. In more detail: To introduce mutation 253A into the gene of SEQ ID NO: 1, we carried out two separate PCRs:

(1) with Primer1:
(SEQ ID NO 45)
GAAATTAATACGACTCACTATAGG
and

253A-Primer2:
(SEQ ID NO: 47)
ATTCAGAATACGAAAACGATATTTACGCGG, (2) with 253A-Primer3:
(SEQ ID NO: 48)
ATCGTTTTCGTATTCTGAATGcTAGCAACACCCGT
and Primer4
(SEQ ID NO: 46)
GGTTATGCTAGTTATTGCTCAGCGGTG.

In both reactions, a recombinant gene encoding SEQ ID NO: 1 was used as the template. Primers 1 and 4 bind inside the vector sequence and are not specific to the recombinant gene. They are therefore used in the mutagenesis procedure of all mutant genes. Primers 2 and 3 are specific for each mutation and bind inside the recombinant gene and their binding sites overlap. The binding site of primer 3 contains the mutation site. Primer 3 comprises the mutated (desired) sequence, which is not 100% matching the template (lower case type font in the primer sequence shown in table 6 indicate the mis-matched nucleotides), however, the primer has enough affinity and specificity to the binding site to produce the desired PCR product. Purified PCR products from reactions (1) and (2) were combined and used as template for PCR reaction with Primer 1 and Primer 4. The product of this reaction, containing the mutant sequence of the gene, was cloned in a plasmid vector for expression in *E. coli*.

For introducing the other mutations, general primers 1 and 4 were used, in combination with specific primers 2 and 3 as listed below in table 6.

TABLE 6

Sequence of primers used in the mutagenesis procedure

| SEQ ID NO: | Name | Sequence |
|---|---|---|
| 45 | Primer 1 | GAAATTAATACGACTCACTATAGG |
| 46 | Primer 4 | GGTTATGCTAGTTATTGCTCAGCGGTG |
| 47 | G253A-Primer2 | ATTCAGAATACGAAAACGATATTTACGCGG |
| 48 | G253A-Primer3 | ATCGTTTTCGTATTCTGAATGcTAGCAACACCCGT |
| 49 | S128P-Primer2 | GCCCACTTCTTTATAATCTTTCGTATACCA |
| 50 | S128D-Primer3 | AAGATTATAAAGAAGTGGGCccCTTCTTCAAAGAA |
| 51 | N384D-Primer2 | CAGCAGCAGCAGAGGACGACCAAAATCATC |

TABLE 6 -continued

Sequence of primers used in the mutagenesis procedure

| SEQ ID NO: | Name | Sequence |
|---|---|---|
| 52 | N384D-Primer3 | GTCGTCCTCTGCTGCTGCTGgACAACAAAAAATGG |
| 53 | H364I-Primer2 | GGTGCTAATTTTGTTATTACGCAGGCTACG |
| 54 | H364I-Primer3 | GTAATAACAAAATTAGCACCatTCGTAATCTGAAA |
| 55 | S292P-Primer2 | TTCAATCGGAATTTTGTTCATCTGCACCGG |
| 56 | S292P-Primer3 | TGAACAAAATTCCGATTGAAccCAGCGAACGCATT |
| 57 | A450P-Primer2 | ACGAGGCGGACCGGTATAGATAATGGTGCC |
| 58 | A450P-Primer3 | TCTATACCGGTCCGCCTCGTccACCGGAACCGAAT |
| 59 | Q33T-Primer2 | GATTTTCACCTCATAATAGTTTTTGCCTTT |
| 60 | Q33T-Primer3 | ACTATTATGAGGTGAAAATCacAGAGTTTAAAAAA |
| 61 | A322P-Primer2 | ATCTGCATCCGGACCCAGATCATTTTTCAG |
| 62 | A322P-Primer3 | ATCTGGGTCCGGATGCAGATcCCGAAGATGAAACC |

Example 2: Heterologous Expression of Variant and Non-Mutated Laccases

Variant or mutated laccases were expressed in *E. coli*, *Bacillus subtilis* and *Pichia pastoris*.

The coding sequences of recombinant laccases were cloned into the pHT43 vector for expression in *Bacillus subtilis* (MoBiTec). pHT43 vector uses the strong promoter preceeding the groESL operon of *B. subtilis* fused to the lac operator allowing induction by addition of IPTG.

The vector encoded a signal peptide from the amyQ gene in frame with the recombinant laccase. Transformation and cultivation of *Bacillus* transformants was done according to MoBiTec's manual.

Cells were grown overnight in 2×YT medium supplemented with 5 µg/ml chloramphenicol and then transferred into fresh 2×YT medium with 5 µg/ml chloramphenicol at an optical density OD600 of about 0.15. When the cultures reached an OD600 of 0.7-0.8, one mM IPTG was added to induce the expression of recombinant protein. Samples were collected at different time points for analysis during induction (t=2.5 h-48 h).

For the analyses, the culture supernatant was collected and intracellular protein was prepared. For this, the cells were harvested by centrifugation (10 min, 6,000×g, 4° C.), and supernatant was collected for analysis. The cell pellets were washed and re-suspend in 50 mM sodium phosphate buffer (pH 7.0) with lysozyme (250 µg/µl). The cells were disrupted by vortexing with glass beads, i.e. bead beating.

Production of the proteins was analyzed using SDS-PAGE, as well as by laccase activity measurements. Active, soluble protein was found only in the supernatant.

Total amount of recombinant protein in the cells and in the supernatant was determined by western blot with anti-His tag antibodies.

For expression in *Pichia Pastoris*, recombinant genes were cloned into a commercial *Pichia Pastoris* expression vector pPICZ-A available from Invitrogen (Life Technologies). This vector provides secreted protein expression under the control of methanol inducible AOX1 promoter upon integration of the construct into genomic DNA of the yeast cell.

Linearized plasmid DNA was introduced into yeast cells by electroporation, and clones with integrated recombinant gene were selected on agar medium plates with Zeocin (25 ug/ml). Ten colonies from each construct were tested in small liquid cultures (3 ml) with 72 hour cultivation in humidified shaker at 28 C according to the Plasmid manufacturer manual (http://tools.lifetechnologies.com/content/sfs/manuals/ppiczalpha_man.pdf). The medium recommended by manufacturer was supplemented with 1 mM CuCl, as laccase protein contains copper as a cofactor. Activity in the medium was measured by DMP (2,6-Dimethoxyphenol) oxidation as detailed in the Examples section, and the two best producing clones were selected for each gene. Parallel cultures of the selected clones were gown in flask scale according to the Plasmid manufacturer manual (see above) at 28 degrees C. for 105 hours. Cells were removed by centrifugation, medium containing the recombinant protein was collected. These preparations were used for comparison of volumetric activities of variant and non-mutated genes.

For recombinant expression in E. coli, recombinant genes were cloned into pET-28 commercial expression vector under the control of T7 bacteriophage promoter. Protein production was carried out in E. coli BL21(DE3) strain according to the plasmid manufacturer protocol http://richsingiser.com/4402/Novagen%20pET%20system%20manual.pdf. The medium recommended by manufacturer was supplemented with 1 mM CuCl2, as laccase protein contains copper as a cofactor. The incubation temperature for protein production was 30 degrees C., which was found optimal for maximum yield of the active protein. Cells were lysed using lysis buffer (50 mM Tris-HCl pH7.4, 1% Triton X100, 1 mM CuCl2) and heated at 70 degrees C. for 20 min. Coagulated cell debris was removed by centrifugation. The recombinant laccase being a thermostable protein remained in soluble fraction. Enzymatic activity was detectable only in soluble fraction. Analysis of soluble and insoluble fractions by gel-electrophoresis revealed that only a very small fraction (less than 1%) of the active recombinant protein according to SEQ ID NO: 1 was present in the soluble fraction. The rest of the recombinant protein was present in the inactive form as insoluble inclusion bodies.

Example 3: Measurement of Yield

The relative yields of mutated and non-mutated soluble laccases were determined by densitometry of protein bands after denaturing polyacrylamide gel electrophoresis. To this end, samples of soluble proteins after thermal treatment (See example 2) obtained from parallel cultures of mutated and non-mutated clones, were analyzed by gel-electrophoresis under denaturing conditions (a standard method well known in the art of molecular biology). After staining the gel with Coomassie Brilliant Blue, the gel was scanned to obtain a bitmap image, and intensity of the band corresponding to recombinant laccase was quantified by ImageJ software (a public freeware developed at National Institute of Health and online available at http://imagej.nih.gov/ij/)

Example 4: Measuring Relative Laccase Activity in Solution by DMP Oxidation

The term "laccase activity" is used herein to mean the capability to act as a laccase enzyme, which may be expressed as the maximal initial rate of the specific oxidation reaction. In some experiments relative activity was measured by oxidation of DMP (2,6-Dimethoxyphenol). Reaction course was monitored by change in absorbance at 468 nm (extinction coefficient of oxidized DMP at 468 nm is 14800 M-1 cm-1). The appropriate reaction time was determined to provide initial rates of oxidation when color development is linear in time. DMP concentration in the reaction mixture was 1 mM to provide maximum initial rates (substrate saturation conditions).

Typically, reactions were carried out in 200 ul in 96-well plates. 180 μl of enzyme dilution in Britton and Robinson buffer (0.04 M $H_3BO_3$, 0.04 M $H_3PO_4$ and 0.04 M $CH_3COOH$ that has been titrated to pH 9.0 with 0.2 M NaOH) was prepared in the assay plate and equilibrated to the room temperature (23 degrees C.), then 20 uL of 10 mM DMP solution was added to start the reaction. The reaction was incubated at room temperature for 5-20 min. After that, optical density at 468 nm was measured using microtiter plate reader. Sample containing no enzyme (only buffer and substrate) was used for background correction, OD reading from this sample was subtracted from all OD values.

In order to determine relative activity of mutated laccase, the absorbance of the reference laccase sample was taken as 100%, and relative activity was determined as fraction of this absorbance.

All enzymes were prepared in parallel production cultures and processed in the same way, so that volumentric activities could be directly compared.

Example 5: Identification of the Amino Acid Position Corresponding to a Certain Position in SEQ ID NO: 1

In order to identify the amino acid position that corresponds to a certain position in SEQ ID NO: 1 in a given sequence X, the sequence X is aligned with the sequence of SEQ ID NO: 1 using standard software available in the art, in this case the "Align" tool at NCBI recourse http://blast.ncbi.nlm.nih.gov/Blast.cgi?PAGE_TYPE=BlastSearch&BLAST_SPEC=blast2seq&LINK_LOC=align2seq.

As an example, sequence SEQ ID NO: 44 was aligned with SEQ ID NO: 1. In the alignment shown below, only a fragment of that alignment is shown, i.e. the fragment corresponding to amino acids 359-386 of SEQ ID NO: 1 and amino acids 361-388 of SEQ ID NO: 44.

```
359 NKISTHRNLKLVGSTDDFGRPLLLLNNK 386 SEQ ID NO: 1
    | ||  ||||||||| |  ||||||||||
361 NQISAYRNLKLVGSQDEYGRPLLLLNNK 388 SEQ ID NO: 44
```

It is immediately evident that this particular region is highly similar in the examined region. For example, the Asparagine (N) residue at position 386 of SEQ ID NO: 44 corresponds to an Asparagine residue at position 384 in SEQ ID NO: 1. The amino acid N in SEQ ID NO: 44 that corresponds to position 384 in SEQ ID NO: 1 is underlined.

The above observations lead to a number of conclusions:

This description provides a nucleic acid encoding a polypeptide with laccase activity (EC 1.10.3.2) comprising an amino acid sequence that is at least 90% identical to the amino acid sequence according to SEQ ID NO: 1, wherein the polypeptide comprises at least one amino acid selected from the group consisting of:

Alanine at a position corresponding to position 253 in SEQ ID NO: 1,

Proline at a position corresponding to position 128 in SEQ ID NO: 1,

Aspartic acid at a position corresponding to position 384 in SEQ ID NO: 1,

Isoleucine at a position corresponding to position 364 in SEQ ID NO: 1,

Proline at a position corresponding to position 292 in SEQ ID NO: 1,

Proline at a position corresponding to position 450 in SEQ ID NO: 1,

Threonine at a position corresponding to position 33 in SEQ ID NO: 1 and

Proline at a position corresponding to position 322 in SEQ ID NO: 1.

The description also provides a nucleic acid as described above wherein said at least one amino acid is at least two amino acids, such as 3, 4, 5, 6, 7 or 8 amino acids.

The description also provides a vector comprising a nucleic acid as described herein.

The description also provides a composition comprising a nucleic acid as described herein or a vector as described herein.

The description also provides a recombinant host cell comprising a nucleic acid as described herein, a vector as described herein or a composition as described herein.

The description also provides a recombinant host cell as described herein selected from the group consisting of *Escherichia coli*, *Bacillus subtilis* and *Pichia pastoris*.

The description also relates to a method for producing a polypeptide, comprising the steps of culturing a recombinant host cell as described herein under conditions suitable for the production of the polypeptide, and recovering the polypeptide obtained, and optionally purifying the polypeptide.

The description also relates to a polypeptide obtainable by a method as described above.

The description also provides for the use of a polypeptide as described above in an application selected from the group consisting of pulp delignification, oxidation of lignin, degrading or decreasing the structural integrity of lignocellulosic material, textile dye bleaching, wastewater detoxification, xenobiotic detoxification, production of a sugar from a lignocellulosic material and recovering cellulose from a biomass.

The description also provides for a method for improving the yield of a soluble polypeptide with laccase activity in a heterologous expression system comprising the step of altering at least one amino acid at a position selected from the group consisting of positions corresponding to positions 253, 128, 384, 364, 292, 450, 33 and 322 in SEQ ID NO: 1 into an Alanine, Proline, Aspartic acid, Isoleucine, Proline, Proline, Threonine and Proline respectively, wherein the polypeptide with laccase activity is a polypeptide with an amino acid sequence according to SEQ ID NO: 1 or a polypeptide with an amino acid sequence that is at least 90% identical to the sequence of SEQ ID NO: 1.

The description also provides for a method as described above wherein said at least one amino acid is at least two amino acids, such as 3, 4, 5, 6, 7 or 8 amino acids.

The description also relates to a polypeptide obtainable by a method as described above wherein the yield of soluble, active mutant polypeptide is increased when it is produced in a bacterial host in comparison to the yield of a wild-type polypeptide, wherein the mutant polypeptide comprises a mutation selected from the group consisting of:

Alanine at a position corresponding to position 253 in SEQ ID NO: 1,

Proline at a position corresponding to position 128 in SEQ ID NO: 1,

Aspartic acid at a position corresponding to position 384 in SEQ ID NO: 1,

Isoleucine at a position corresponding to position 364 in SEQ ID NO: 1,

Proline at a position corresponding to position 292 in SEQ ID NO: 1,

Proline at a position corresponding to position 450 in SEQ ID NO: 1,

Threonine at a position corresponding to position 33 in SEQ ID NO: 1 and

Proline at a position corresponding to position 322 in SEQ ID NO: 1, and wherein the mutant polypeptide is otherwise identical to the wild-type polypeptide.

The description also provides a mutant polypeptide with laccase activity (EC 1.10.3.2) comprising an amino acid sequence that is at least 90% identical to the amino acid sequence according to SEQ ID NO: 1, wherein the polypeptide comprises at least one amino acid selected from the group consisting of:

Alanine at a position corresponding to position 253 in SEQ ID NO: 1,

Proline at a position corresponding to position 128 in SEQ ID NO: 1,

Aspartic acid at a position corresponding to position 384 in SEQ ID NO: 1,

Isoleucine at a position corresponding to position 364 in SEQ ID NO: 1,

Proline at a position corresponding to position 292 in SEQ ID NO: 1,

Proline at a position corresponding to position 450 in SEQ ID NO: 1,

Threonine at a position corresponding to position 33 in SEQ ID NO: 1 and

Proline at a position corresponding to position 322 in SEQ ID NO: 1, wherein the mutant polypeptide has an increased yield of active, soluble protein when produced in a bacterial host as compared to the yield of active, soluble protein when the wild-type polypeptide is expressed in the same host, wherein the wild-type polypeptide has an identical amino acid sequence as the mutant polypeptide, except for any of the above mentioned mutations.

REFERENCES

1. Martins L O, Soares C M, Pereira M M, Teixeira M, Costa T, Jones G H, et al. Molecular and biochemical characterization of a highly stable bacterial laccase that occurs as a structural component of the *Bacillus subtilis* endospore coat. J Biol Chem 2002; 277:18849-59.
2. Bento I, Martins L O, Gato Lopes G, Arménia Carrondo M, Lindley P F. Dioxygen reduction by multi-copper oxidases; a structural perspective. Dalton Trans 2005; 21:3507-13.
3. Brissos V, Pereira L, Munteanu F D, Cavaco-Paulo A, Martins L O. Expression system of CotA-laccase for directed evolution and high-throughput screenings for the oxidation of high-redox potential dyes. Biotechnol J 2009; 4:558-63.
4. Suzuki T, Endo K, Ito M, Tsujibo H, Miyamoto K, Inamori Y. A thermostable laccase from *Streptomyces lavendulae* REN-7: purification, characterization, nucleotide sequence and expression. Biosci Biotechnol Biochem 2003; 67:2167-75.

5. Kumar et al., "Combined sequence and structure analysis of the fungal laccase family", Biotechnol. Bioeng., 83, 386-394, 2003;
6. Morozova et al., "Blue laccases", Biochemistry (Moscow), 72, 1136-1150, 2007).
7. Koschorreck, K., Richter, S. M., Ene, A. B., Roduner, E., Schmid, R. D., and Urlacher, V. B. (2008). Cloning and characterization of a new laccase from *Bacillus licheniformis* catalyzing dimerization of phenolic acids. Appl. Microbiol. Biotechnol. 79, 217-224.
8. Methods in Molecular Biology, Vol 182, "In vitro mutagenesis protocols", Eds Jeff Braman, Humana Press 2002)

The invention claimed is:

1. A polypeptide with laccase activity (EC 1.10.3.2) comprising an amino acid sequence that is at least 90% identical to the full length of the amino acid sequence according to SEQ ID NO: 1, wherein the polypeptide comprises at least one amino acid selected from the group consisting of:
Alanine at a position corresponding to position 253 in SEQ ID NO: 1,
Proline at a position corresponding to position 128 in SEQ ID NO: 1,
Aspartic acid at a position corresponding to position 384 in SEQ ID NO: 1,
Isoleucine at a position corresponding to position 364 in SEQ ID NO: 1,
Proline at a position corresponding to position 292 in SEQ ID NO: 1,
Proline at a position corresponding to position 450 in SEQ ID NO: 1,
Threonine at a position corresponding to position 33 in SEQ ID NO: 1 and
Proline at a position corresponding to position 322 in SEQ ID NO: 1.

2. The polypeptide of claim 1 wherein the polypeptide comprises at least two amino acids selected from the group consisting of:
Alanine at a position corresponding to position 253 in SEQ ID NO: 1,
Proline at a position corresponding to position 128 in SEQ ID NO: 1,
Aspartic acid at a position corresponding to position 384 in SEQ ID NO: 1,
Isoleucine at a position corresponding to position 364 in SEQ ID NO: 1, Proline at a position corresponding to position 292 in SEQ ID NO: 1,
Proline at a position corresponding to position 450 in SEQ ID NO: 1,
Threonine at a position corresponding to position 33 in SEQ ID NO: 1 and
Proline at a position corresponding to position 322 in SEQ ID NO: 1.

3. The polypeptide of claim 1, wherein the polypeptide is produced in *E. coli*.

4. The polypepetide of claim 1 wherein the polypeptide is an isolated polypeptide.

5. A composition comprising the polypeptide according to claim 1.

6. A nucleic acid encoding the polypeptide according to claim 1.

7. The nucleic acid according to claim 6, wherein the nucleic acid is comprised in a vector.

8. The nucleic acid of claim 6, wherein the nucleic acid is comprised in a composition.

9. The nucleic acid according to claim 6, wherein the nucleic acid is comprised in a host cell.

10. The nucleic acid according to claim 9, wherein the host cell is selected from the group consisting of *Escherichia coli, Bacillus, Corynebacterium, Pseudomonas, Pichia pastoris, Saccharomyces cerevisiae, Yarrowia lipolytica*, filamentous fungi, yeast and insect cells.

11. A method for altering a polypeptide with laccase activity comprising the step of altering at least one amino acid at a position selected from the group consisting of positions corresponding to positions 253, 128, 384, 364, 292, 450, 33 and 322 in SEQ ID NO: 1 into an Alanine, Proline, Aspartic acid, Isoleucine, Proline, Proline, Threonine and Proline respectively, wherein the polypeptide with laccase activity is a polypeptide comprising SEQ ID NO: 1 or a polypeptide with an amino acid sequence that is at least 90% identical to the full length of the sequence of SEQ ID NO: 1.

12. The method according to claim 11 wherein the method comprises altering at least two amino acids at positions selected from the group consisting of positions corresponding to positions 253, 128, 384, 364, 292, 450, 33 and 322 in SEQ ID NO: 1 into an Alanine, Proline, Aspartic acid, Isoleucine, Proline, Proline, Threonine and Proline respectively.

13. The polypeptide of claim 1 wherein the polypeptide comprises at least three amino acids selected from the group consisting of:
Alanine at a position corresponding to position 253 in SEQ ID NO: 1,
Proline at a position corresponding to position 128 in SEQ ID NO: 1,
Aspartic acid at a position corresponding to position 384 in SEQ ID NO: 1,
Isoleucine at a position corresponding to position 364 in SEQ ID NO: 1,
Proline at a position corresponding to position 292 in SEQ ID NO: 1,
Proline at a position corresponding to position 450 in SEQ ID NO: 1,
Threonine at a position corresponding to position 33 in SEQ ID NO: 1 and
Proline at a position corresponding to position 322 in SEQ ID NO: 1.

14. The polypeptide of claim 1 wherein the polypeptide comprises at least four amino acids selected from the group consisting of:
Alanine at a position corresponding to position 253 in SEQ ID NO: 1,
Proline at a position corresponding to position 128 in SEQ ID NO: 1,
Aspartic acid at a position corresponding to position 384 in SEQ ID NO: 1,
Isoleucine at a position corresponding to position 364 in SEQ ID NO: 1,
Proline at a position corresponding to position 292 in SEQ ID NO: 1,
Proline at a position corresponding to position 450 in SEQ ID NO: 1,
Threonine at a position corresponding to position 33 in SEQ ID NO: 1 and
Proline at a position corresponding to position 322 in SEQ ID NO: 1.

15. The polypeptide of claim 1 wherein the polypeptide comprises at least six amino acids selected from the group consisting of:
Alanine at a position corresponding to position 253 in SEQ ID NO: 1,
Proline at a position corresponding to position 128 in SEQ ID NO: 1,
Aspartic acid at a position corresponding to position 384 in SEQ ID NO: 1,
Isoleucine at a position corresponding to position 364 in SEQ ID NO: 1,
Proline at a position corresponding to position 292 in SEQ ID NO: 1,
Proline at a position corresponding to position 450 in SEQ ID NO: 1,
Threonine at a position corresponding to position 33 in SEQ ID NO: 1 and
Proline at a position corresponding to position 322 in SEQ ID NO: 1.

16. The polypeptide of claim 1 wherein the polypeptide is at least 95% identical to full length of SEQ ID NO:1.

17. The method according to claim 12 wherein the method comprises altering at least three amino acids at positions selected from the group consisting of positions corresponding to positions 253, 128, 384, 364, 292, 450, 33 and 322 in SEQ ID NO: 1 into an Alanine, Proline, Aspartic acid, Isoleucine, Proline, Proline, Threonine and Proline respectively.

18. The method according to claim 12 wherein the method comprises altering at least four amino acids at positions selected from the group consisting of positions corresponding to positions 253, 128, 384, 364, 292, 450, 33 and 322 in SEQ ID NO: 1 into an Alanine, Proline, Aspartic acid, Isoleucine, Proline, Proline, Threonine and Proline respectively.

19. The method according to claim 12 wherein the method comprises altering at least six amino acids at positions selected from the group consisting of positions corresponding to positions 253, 128, 384, 364, 292, 450, 33 and 322 in SEQ ID NO: 1 into an Alanine, Proline, Aspartic acid, Isoleucine, Proline, Proline, Threonine and Proline respectively.

20. The method according to claim 12 wherein the polypeptide with laccase activity is a polypeptide is at least 95% identical to the full length SEQ ID NO: 1.

* * * * *

SEQUENCE LISTING

```
<160> NUMBER OF SEQ ID NOS: 67

<210> SEQ ID NO 1
<211> LENGTH: 512
<212> TYPE: PRT
<213> ORGANISM: Bacillus wakoensis

<400> SEQUENCE: 1

Met Arg Arg Lys Leu Glu Lys Phe Val Asp Ser Leu Pro Ile Met Glu
1               5                  10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320
```

```
Asp Ala Glu Asp Glu Thr Asn Glu Ile Met Lys Phe Lys Val Ser Lys
            325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
            355                 360                 365

Leu Val Gly Ser Thr Asp Asp Phe Gly Arg Pro Leu Leu Leu Leu Asn
            370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
            405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
            435                 440                 445

Arg Ala Pro Glu Pro Asn Glu Arg Gly Trp Lys Asp Thr Val Ser Ala
            450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
            485                 490                 495

Met Met Arg Pro Met Lys Val Ile Asp Pro Lys Gln Arg Lys Asp Lys
            500                 505                 510

<210> SEQ ID NO 2
<211> LENGTH: 512
<212> TYPE: PRT
<213> ORGANISM: Bacillus wakoensis

<400> SEQUENCE: 2

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
            35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
            85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
            115                 120                 125

Phe Phe Lys Glu Glu Val Tyr Arg Tyr Leu Asn Glu Gln Arg Ala Met
            130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
            165                 170                 175

Ser Leu Asn Leu Pro Glu Gly Glu Tyr Glu Val Pro Leu Ile Ile Gln
```

```
            180                 185                 190
Asp Arg Thr Phe Asn Glu Asp Gly Ser Leu Phe Tyr Pro Thr Gly Pro
                195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asn
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 3
<211> LENGTH: 512
<212> TYPE: PRT
<213> ORGANISM: Bacillus wakoensis

<400> SEQUENCE: 3

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45
```

```
Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Pro
            115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
                180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
        290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asn
370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
```

```
              465                 470                 475                 480
Gly Asn Tyr Val Trp His Cys His Ile Leu Glu His Glu Asp His Asp
                    485                 490                 495
Met Met Arg Pro Met Lys Val Ile Asp Pro Lys Gln Arg Lys Asp Lys
                    500                 505                 510

<210> SEQ ID NO 4
<211> LENGTH: 512
<212> TYPE: PRT
<213> ORGANISM: Bacillus wakoensis

<400> SEQUENCE: 4

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
                20                  25                  30

Gln Glu Phe Lys Lys Lys Leu His Arg Asp Leu Pro Pro Thr Thr Leu
            35                  40                  45

Trp Gly Tyr Asn Ala Gln Phe Pro Gly Pro Thr Ile Glu Ala Asn Ser
        50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Ser
            115                 120                 125

Phe Phe Lys Glu Glu Val Tyr Arg Tyr Leu Asn Glu Gln Arg Ala Met
        130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
                180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
        210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
            290                 295                 300

Cys Asp Gly Asp Glu Ile Val Leu Lys Asn Asp Leu Gly Pro Asp Ala
305                 310                 315                 320

Asp Ala Glu Asp Glu Thr Asn Gly Ile Met Lys Phe Lys Val Ser Lys
                325                 330                 335
```

```
Pro Leu Lys Glu Lys Asp Thr Ser Val Ile Pro Lys Arg Leu Ser Thr
                340                 345                 350

Ile Arg Ser Leu Arg Asn Asn Lys Ile Ser Thr His Arg Asn Leu Lys
            355                 360                 365

Leu Val Gly Ser Thr Asp Asp Phe Gly Arg Pro Leu Leu Leu Leu Asp
        370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 5
<211> LENGTH: 512
<212> TYPE: PRT
<213> ORGANISM: Bacillus wakoensis

<400> SEQUENCE: 5

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
                20                  25                  30

Gln Glu Phe Lys Lys Lys Leu His Arg Asp Leu Pro Pro Thr Thr Leu
            35                  40                  45

Trp Gly Tyr Asn Ala Gln Phe Pro Gly Pro Thr Ile Glu Ala Asn Ser
        50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205
```

```
Glu Asp Gly Gly Glu Asp Leu Pro Asn Pro Ser Ile Val Pro Ala Phe
        210                 215                 220
Leu Gly Asp Thr Val Leu Val Asn Gly Lys Val Trp Pro Tyr Leu Glu
225                 230                 235                 240
Val Glu Pro Arg Lys Tyr Arg Phe Arg Ile Leu Asn Gly Ser Asn Thr
                245                 250                 255
Arg Ser Tyr Gln Leu His Leu Asp Ser Asn Gln Glu Val Tyr Gln Ile
            260                 265                 270
Gly Ser Asp Gly Gly Leu Leu Glu Lys Pro Val Gln Met Asn Lys Ile
        275                 280                 285
Pro Ile Glu Ser Ser Glu Arg Ile Asp Val Ile Asp Phe Ser Gln
    290                 295                 300
Cys Asp Gly Asp Glu Ile Val Leu Lys Asn Asp Leu Gly Pro Asp Ala
305                 310                 315                 320
Asp Ala Glu Asp Glu Thr Asn Glu Ile Met Lys Phe Lys Val Ser Lys
                325                 330                 335
Pro Leu Lys Glu Lys Asp Thr Ser Val Ile Pro Lys Arg Leu Ser Thr
            340                 345                 350
Ile Arg Ser Leu Arg Asn Asn Lys Ile Ser Thr Ile Arg Asn Leu Lys
        355                 360                 365
Leu Val Gly Ser Thr Asp Asp Phe Gly Arg Pro Leu Leu Leu Leu Asn
370                 375                 380
Asn Lys Lys Trp Ala Asp Pro Thr Thr Glu Lys Pro Lys Val Gly Asp
385                 390                 395                 400
Thr Glu Val Trp Ser Phe Ile Asn Thr Thr Asp Phe Ala His Pro Met
                405                 410                 415
His Ile His Leu Ile His Phe Gln Val Leu Asp Arg Gln Pro Phe Asp
            420                 425                 430
Leu Glu Arg Tyr Asn His Asp Gly Thr Ile Ile Tyr Thr Gly Pro Pro
        435                 440                 445
Arg Ala Pro Glu Pro Asn Glu Arg Gly Trp Lys Asp Thr Val Ser Ala
    450                 455                 460
Pro Ala Gly Gln Ile Thr Arg Val Ile Gly Thr Phe Ala Pro Tyr Thr
465                 470                 475                 480
Gly Asn Tyr Val Trp His Cys His Ile Leu Glu His Glu Asp His Asp
                485                 490                 495
Met Met Arg Pro Met Lys Val Ile Asp Pro Lys Gln Arg Lys Asp Lys
            500                 505                 510

<210> SEQ ID NO 6
<211> LENGTH: 512
<212> TYPE: PRT
<213> ORGANISM: Bacillus wakoensis

<400> SEQUENCE: 6

Met Arg Arg Lys Leu Glu Lys Phe Val Asp Ser Leu Pro Ile Met Glu
1               5                   10                  15
Thr Leu Gln Pro Lys Thr Lys Gly Lys Asn Tyr Tyr Glu Val Lys Ile
            20                  25                  30
Gln Glu Phe Lys Lys Lys Leu His Arg Asp Leu Pro Pro Thr Thr Leu
        35                  40                  45
Trp Gly Tyr Asn Ala Gln Phe Pro Gly Pro Thr Ile Glu Ala Asn Ser
    50                  55                  60
Asn Glu Pro Val Glu Val Lys Trp Ile Asn Glu Leu Pro Asn Lys His
```

```
                65                  70                  75                  80
        Phe Leu Pro Val Asp Trp Ser Ile Met Asn Lys Asp Leu Pro Glu Val
                            85                  90                  95

Arg His Val Thr His Leu His Gly Gly Arg Thr Pro Trp Val Ser Asp
                        100                 105                 110

Gly Tyr Pro Glu Ala Trp Tyr Thr Lys Asp Tyr Lys Glu Val Gly Ser
                    115                 120                 125

Phe Phe Lys Glu Val Tyr Arg Tyr Leu Asn Glu Gln Arg Ala Met
                130                 135                 140

Met Leu Trp Tyr His Asp His Thr Met Gly Ile Thr Arg Leu Asn Asn
        145                 150                 155                 160

Tyr Ala Gly Leu Ala Gly Ala Tyr Ile Ile Arg Asp Lys His Glu Lys
                            165                 170                 175

Ser Leu Asn Leu Pro Glu Gly Glu Tyr Glu Val Pro Leu Ile Ile Gln
                        180                 185                 190

Asp Arg Thr Phe Asn Glu Asp Gly Ser Leu Phe Tyr Pro Thr Gly Pro
                    195                 200                 205

Glu Asp Gly Gly Glu Asp Leu Pro Asn Pro Ser Ile Val Pro Ala Phe
                210                 215                 220

Leu Gly Asp Thr Val Leu Val Asn Gly Lys Val Trp Pro Tyr Leu Glu
        225                 230                 235                 240

Val Glu Pro Arg Lys Tyr Arg Phe Arg Ile Leu Asn Gly Ser Asn Thr
                            245                 250                 255

Arg Ser Tyr Gln Leu His Leu Asp Ser Asn Gln Glu Val Tyr Gln Ile
                        260                 265                 270

Gly Ser Asp Gly Gly Leu Leu Glu Lys Pro Val Gln Met Asn Lys Ile
                    275                 280                 285

Pro Ile Glu Pro Ser Glu Arg Ile Asp Val Ile Asp Phe Ser Gln
                290                 295                 300

Cys Asp Gly Asp Glu Ile Val Leu Lys Asn Asp Leu Gly Pro Asp Ala
        305                 310                 315                 320

Asp Ala Glu Asp Glu Thr Asn Glu Ile Met Lys Phe Lys Val Ser Lys
                            325                 330                 335

Pro Leu Lys Glu Lys Asp Thr Ser Val Ile Pro Lys Arg Leu Ser Thr
                        340                 345                 350

Ile Arg Ser Leu Arg Asn Asn Lys Ile Ser Thr His Arg Asn Leu Lys
                    355                 360                 365

Leu Val Gly Ser Thr Asp Asp Phe Gly Arg Pro Leu Leu Leu Asn
                370                 375                 380

Asn Lys Lys Trp Ala Asp Pro Thr Thr Glu Lys Pro Lys Val Gly Asp
        385                 390                 395                 400

Thr Glu Val Trp Ser Phe Ile Asn Thr Thr Asp Phe Ala His Pro Met
                            405                 410                 415

His Ile His Leu Ile His Phe Gln Val Leu Asp Arg Gln Pro Phe Asp
                        420                 425                 430

Leu Glu Arg Tyr Asn His Asp Gly Thr Ile Ile Tyr Thr Gly Pro Pro
                    435                 440                 445

Arg Ala Pro Glu Pro Asn Glu Arg Gly Trp Lys Asp Thr Val Ser Ala
                450                 455                 460

Pro Ala Gly Gln Ile Thr Arg Val Ile Gly Thr Phe Ala Pro Tyr Thr
        465                 470                 475                 480

Gly Asn Tyr Val Trp His Cys His Ile Leu Glu His Glu Asp His Asp
                            485                 490                 495
```

```
Met Met Arg Pro Met Lys Val Ile Asp Pro Lys Gln Arg Lys Asp Lys
            500                 505                 510

<210> SEQ ID NO 7
<211> LENGTH: 512
<212> TYPE: PRT
<213> ORGANISM: Bacillus wakoensis

<400> SEQUENCE: 7

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
```

```
                355                 360                 365
Leu Val Gly Ser Thr Asp Asp Phe Gly Arg Pro Leu Leu Leu Asn
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Pro Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 8
<211> LENGTH: 512
<212> TYPE: PRT
<213> ORGANISM: Bacillus wakoensis

<400> SEQUENCE: 8

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Thr Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220
```

```
Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asn
370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 9
<211> LENGTH: 512
<212> TYPE: PRT
<213> ORGANISM: Bacillus wakoensis

<400> SEQUENCE: 9

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
                20                  25                  30

Gln Glu Phe Lys Lys Lys Leu His Arg Asp Leu Pro Pro Thr Thr Leu
            35                  40                  45

Trp Gly Tyr Asn Ala Gln Phe Pro Gly Pro Thr Ile Glu Ala Asn Ser
        50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95
```

```
Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
            115                 120                 125

Phe Phe Lys Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
            245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
            275                 280                 285

Pro Ile Glu Ser Ser Glu Arg Ile Asp Val Ile Ile Asp Phe Ser Gln
            290                 295                 300

Cys Asp Gly Asp Glu Ile Val Leu Lys Asn Asp Leu Gly Pro Asp Ala
305                 310                 315                 320

Asp Pro Glu Asp Glu Thr Asn Glu Ile Met Lys Phe Lys Val Ser Lys
            325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
            355                 360                 365

Leu Val Gly Ser Thr Asp Asp Phe Gly Arg Pro Leu Leu Leu Leu Asn
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
    435                 440                 445

Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510
```

<210> SEQ ID NO 10
<211> LENGTH: 512
<212> TYPE: PRT
<213> ORGANISM: Bacillus wakoensis

<400> SEQUENCE: 10

```
Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Pro
        115                 120                 125

Phe Phe Lys Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asn
    370                 375                 380
```

```
Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
            405                 410                 415

His Ile His Leu Ile His Phe Gln Val Leu Asp Arg Gln Pro Phe Asp
        420                 425                 430

Leu Glu Arg Tyr Asn His Asp Gly Thr Ile Ile Tyr Thr Gly Pro Pro
    435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510
```

<210> SEQ ID NO 11
<211> LENGTH: 512
<212> TYPE: PRT
<213> ORGANISM: Bacillus wakoensis

<400> SEQUENCE: 11

```
Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Gly Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
```

```
                    245                 250                 255
Arg Ser Tyr Gln Leu His Leu Asp Ser Asn Gln Glu Val Tyr Gln Ile
        260                 265                 270
Gly Ser Asp Gly Gly Leu Leu Glu Lys Pro Val Gln Met Asn Lys Ile
        275                 280                 285
Pro Ile Glu Ser Ser Glu Arg Ile Asp Val Ile Asp Phe Ser Gln
        290                 295                 300
Cys Asp Gly Asp Glu Ile Val Leu Lys Asn Asp Leu Gly Pro Asp Ala
305                 310                 315                 320
Asp Ala Glu Asp Glu Thr Asn Glu Ile Met Lys Phe Lys Val Ser Lys
                325                 330                 335
Pro Leu Lys Glu Lys Asp Thr Ser Val Ile Pro Lys Arg Leu Ser Thr
            340                 345                 350
Ile Arg Ser Leu Arg Asn Asn Lys Ile Ser Thr His Arg Asn Leu Lys
                355                 360                 365
Leu Val Gly Ser Thr Asp Asp Phe Gly Arg Pro Leu Leu Leu Leu Asp
        370                 375                 380
Asn Lys Lys Trp Ala Asp Pro Thr Thr Glu Lys Pro Lys Val Gly Asp
385                 390                 395                 400
Thr Glu Val Trp Ser Phe Ile Asn Thr Thr Asp Phe Ala His Pro Met
                405                 410                 415
His Ile His Leu Ile His Phe Gln Val Leu Asp Arg Gln Pro Phe Asp
            420                 425                 430
Leu Glu Arg Tyr Asn His Asp Gly Thr Ile Ile Tyr Thr Gly Pro Pro
        435                 440                 445
Arg Ala Pro Glu Pro Asn Glu Arg Gly Trp Lys Asp Thr Val Ser Ala
    450                 455                 460
Pro Ala Gly Gln Ile Thr Arg Val Ile Gly Thr Phe Ala Pro Tyr Thr
465                 470                 475                 480
Gly Asn Tyr Val Trp His Cys His Ile Leu Glu His Glu Asp His Asp
                485                 490                 495
Met Met Arg Pro Met Lys Val Ile Asp Pro Lys Gln Arg Lys Asp Lys
            500                 505                 510

<210> SEQ ID NO 12
<211> LENGTH: 512
<212> TYPE: PRT
<213> ORGANISM: Bacillus wakoensis

<400> SEQUENCE: 12

Met Arg Arg Lys Leu Glu Lys Phe Val Asp Ser Leu Pro Ile Met Glu
1               5                   10                  15
Thr Leu Gln Pro Lys Thr Lys Gly Lys Asn Tyr Tyr Glu Val Lys Ile
            20                  25                  30
Gln Glu Phe Lys Lys Lys Leu His Arg Asp Leu Pro Pro Thr Thr Leu
        35                  40                  45
Trp Gly Tyr Asn Ala Gln Phe Pro Gly Pro Thr Ile Glu Ala Asn Ser
    50                  55                  60
Asn Glu Pro Val Glu Val Lys Trp Ile Asn Glu Leu Pro Asn Lys His
65                  70                  75                  80
Phe Leu Pro Val Asp Trp Ser Ile Met Asn Lys Asp Leu Pro Glu Val
                85                  90                  95
Arg His Val Thr His Leu His Gly Gly Arg Thr Pro Trp Val Ser Asp
            100                 105                 110
```

Gly Tyr Pro Glu Ala Trp Tyr Thr Lys Asp Tyr Lys Glu Val Gly Ser
            115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr Ile Arg Asn Leu Lys
        355                 360                 365

Leu Val Gly Ser Thr Asp Asp Phe Gly Arg Pro Leu Leu Leu Leu Asn
370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 13
<211> LENGTH: 512
<212> TYPE: PRT

<213> ORGANISM: Bacillus wakoensis

<400> SEQUENCE: 13

```
Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Pro Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asn
    370                 375                 380

Asn Lys Lys Trp Ala Asp Pro Thr Thr Glu Lys Pro Lys Val Gly Asp
385                 390                 395                 400
```

```
Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510
```

<210> SEQ ID NO 14
<211> LENGTH: 512
<212> TYPE: PRT
<213> ORGANISM: Bacillus wakoensis

<400> SEQUENCE: 14

```
Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270
```

```
Gly Ser Asp Gly Gly Leu Leu Glu Lys Pro Val Gln Met Asn Lys Ile
            275                 280                 285

Pro Ile Glu Ser Ser Glu Arg Ile Asp Val Ile Ile Asp Phe Ser Gln
290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
            355                 360                 365

Leu Val Gly Ser Thr Asp Asp Phe Gly Arg Pro Leu Leu Leu Leu Asn
        370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Pro Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 15
<211> LENGTH: 512
<212> TYPE: PRT
<213> ORGANISM: Bacillus wakoensis

<400> SEQUENCE: 15

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Thr Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
```

```
            130                 135                 140
Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
                195                 200                 205

Glu Asp Gly Gly Glu Asp Leu Pro Asn Pro Ser Ile Val Pro Ala Phe
            210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
                260                 265                 270

Gly Ser Asp Gly Gly Leu Leu Glu Lys Pro Val Gln Met Asn Lys Ile
            275                 280                 285

Pro Ile Glu Ser Ser Glu Arg Ile Asp Val Ile Ile Asp Phe Ser Gln
290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
                355                 360                 365

Leu Val Gly Ser Thr Asp Asp Phe Gly Arg Pro Leu Leu Leu Leu Asn
370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
                420                 425                 430

Leu Glu Arg Tyr Asn His Asp Gly Thr Ile Ile Tyr Thr Gly Pro Pro
            435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 16
<211> LENGTH: 512
<212> TYPE: PRT
<213> ORGANISM: Bacillus wakoensis

<400> SEQUENCE: 16
```

-continued

```
Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
            35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
            115                 120                 125

Phe Phe Lys Glu Val Tyr Arg Tyr Leu Asn Glu Gln Arg Ala Met
            130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
            210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
            275                 280                 285

Pro Ile Glu Ser Ser Glu Arg Ile Asp Val Ile Ile Asp Phe Ser Gln
            290                 295                 300

Cys Asp Gly Asp Glu Ile Val Leu Lys Asn Asp Leu Gly Pro Asp Ala
305                 310                 315                 320

Asp Pro Glu Asp Glu Thr Asn Glu Ile Met Lys Phe Lys Val Ser Lys
            325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
            355                 360                 365

Leu Val Gly Ser Thr Asp Asp Phe Gly Arg Pro Leu Leu Leu Leu Asn
            370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
```

```
            420                 425                 430
Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 17
<211> LENGTH: 512
<212> TYPE: PRT
<213> ORGANISM: Bacillus wakoensis

<400> SEQUENCE: 17

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Pro
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285
```

```
Pro Ile Glu Ser Ser Glu Arg Ile Asp Val Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
                340                 345                 350

Ile Arg Ser Leu Arg Asn Asn Lys Ile Ser Thr His Arg Asn Leu Lys
            355                 360                 365

Leu Val Gly Ser Thr Asp Asp Phe Gly Arg Pro Leu Leu Leu Asp
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
    435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510

<210> SEQ ID NO 18
<211> LENGTH: 512
<212> TYPE: PRT
<213> ORGANISM: Bacillus wakoensis

<400> SEQUENCE: 18

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
                20                  25                  30

Gln Glu Phe Lys Lys Lys Leu His Arg Asp Leu Pro Pro Thr Thr Leu
            35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Pro
            115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160
```

Tyr Ala Gly Leu Ala Gly Ala Tyr Ile Ile Arg Asp Lys His Glu Lys
            165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
            245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
            275                 280                 285

Pro Ile Glu Ser Ser Glu Arg Ile Asp Val Ile Ile Asp Phe Ser Gln
            290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
            325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr Ile Arg Asn Leu Lys
            355                 360                 365

Leu Val Gly Ser Thr Asp Asp Phe Gly Arg Pro Leu Leu Leu Asn
            370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
            405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
            435                 440                 445

Arg Ala Pro Glu Pro Asn Glu Arg Gly Trp Lys Asp Thr Val Ser Ala
            450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
            485                 490                 495

Met Met Arg Pro Met Lys Val Ile Asp Pro Lys Gln Arg Lys Asp Lys
            500                 505                 510

<210> SEQ ID NO 19
<211> LENGTH: 512
<212> TYPE: PRT
<213> ORGANISM: Bacillus wakoensis

<400> SEQUENCE: 19

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile

```
                    20                  25                  30
Gln Glu Phe Lys Lys Lys Leu His Arg Asp Leu Pro Pro Thr Thr Leu
                35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Pro
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Pro Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Asn
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445
```

```
Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 20
<211> LENGTH: 512
<212> TYPE: PRT
<213> ORGANISM: Bacillus wakoensis

<400> SEQUENCE: 20

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Pro
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
```

```
            305                 310                 315                 320
Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
                340                 345                 350

Ile Arg Ser Leu Arg Asn Asn Lys Ile Ser Thr His Arg Asn Leu Lys
                355                 360                 365

Leu Val Gly Ser Thr Asp Asp Phe Gly Arg Pro Leu Leu Leu Asn
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
                420                 425                 430

Leu Glu Arg Tyr Asn His Asp Gly Thr Ile Ile Tyr Thr Gly Pro Pro
            435                 440                 445

Arg Pro Pro Glu Pro Asn Glu Arg Gly Trp Lys Asp Thr Val Ser Ala
        450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510

<210> SEQ ID NO 21
<211> LENGTH: 512
<212> TYPE: PRT
<213> ORGANISM: Bacillus wakoensis

<400> SEQUENCE: 21

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
                20                  25                  30

Thr Glu Phe Lys Lys Lys Leu His Arg Asp Leu Pro Pro Thr Thr Leu
            35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Pro
            115                 120                 125

Phe Phe Lys Glu Glu Val Tyr Arg Tyr Leu Asn Glu Gln Arg Ala Met
        130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175
```

```
Ser Leu Asn Leu Pro Glu Gly Glu Tyr Val Pro Leu Ile Ile Gln
            180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asn
370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 22
<211> LENGTH: 512
<212> TYPE: PRT
<213> ORGANISM: Bacillus wakoensis

<400> SEQUENCE: 22

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45
```

-continued

Trp Gly Tyr Asn Ala Gln Phe Pro Gly Pro Thr Ile Glu Ala Asn Ser
 50                  55                  60

Asn Glu Pro Val Glu Val Lys Trp Ile Asn Glu Leu Pro Asn Lys His
 65                  70                  75                  80

Phe Leu Pro Val Asp Trp Ser Ile Met Asn Lys Asp Leu Pro Glu Val
                 85                  90                  95

Arg His Val Thr His Leu His Gly Arg Thr Pro Trp Val Ser Asp
                100                 105                 110

Gly Tyr Pro Glu Ala Trp Tyr Thr Lys Asp Tyr Lys Glu Val Gly Pro
            115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
                180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
            275                 280                 285

Pro Ile Glu Ser Ser Glu Arg Ile Asp Val Ile Ile Asp Phe Ser Gln
290                 295                 300

Cys Asp Gly Asp Glu Ile Val Leu Lys Asn Asp Leu Gly Pro Asp Ala
305                 310                 315                 320

Asp Pro Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
            355                 360                 365

Leu Val Gly Ser Thr Asp Asp Phe Gly Arg Pro Leu Leu Leu Leu Asn
370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
            435                 440                 445

Arg Ala Pro Glu Pro Asn Glu Arg Gly Trp Lys Asp Thr Val Ser Ala
450                 455                 460

```
Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 23
<211> LENGTH: 512
<212> TYPE: PRT
<213> ORGANISM: Bacillus wakoensis

<400> SEQUENCE: 23

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335
```

```
Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr Ile Arg Asn Leu Lys
        355                 360                 365

Leu Val Gly Ser Thr Asp Asp Phe Gly Arg Pro Leu Leu Leu Leu Asp
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 24
<211> LENGTH: 512
<212> TYPE: PRT
<213> ORGANISM: Bacillus wakoensis

<400> SEQUENCE: 24

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
```

```
                195                 200                 205
Glu Asp Gly Gly Glu Asp Leu Pro Asn Pro Ser Ile Val Pro Ala Phe
            210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Pro Ser Glu Arg Ile Asp Val Ile Asp Phe Ser Gln
290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Asp
370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 25
<211> LENGTH: 512
<212> TYPE: PRT
<213> ORGANISM: Bacillus wakoensis

<400> SEQUENCE: 25

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60
```

```
Asn Glu Pro Val Glu Val Lys Trp Ile Asn Glu Leu Pro Asn Lys His
 65                  70                  75                  80

Phe Leu Pro Val Asp Trp Ser Ile Met Asn Lys Asp Leu Pro Glu Val
                 85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asp
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Pro Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
```

```
                    485                 490                 495
Met Met Arg Pro Met Lys Val Ile Asp Pro Lys Gln Arg Lys Asp Lys
                500                 505                 510

<210> SEQ ID NO 26
<211> LENGTH: 512
<212> TYPE: PRT
<213> ORGANISM: Bacillus wakoensis

<400> SEQUENCE: 26

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Thr Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Val Ile Pro Lys Arg Leu Ser Thr
            340                 345                 350
```

-continued

```
Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asp
        370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
                420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
        450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510

<210> SEQ ID NO 27
<211> LENGTH: 512
<212> TYPE: PRT
<213> ORGANISM: Bacillus wakoensis

<400> SEQUENCE: 27

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
                20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65              70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
        130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Tyr Glu Val Pro Leu Ile Ile Gln
                180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220
```

```
Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
            245                 250                 255

Arg Ser Tyr Gln Leu His Leu Asp Ser Asn Gln Glu Val Tyr Gln Ile
                260                 265                 270

Gly Ser Asp Gly Gly Leu Leu Glu Lys Pro Val Gln Met Asn Lys Ile
            275                 280                 285

Pro Ile Glu Ser Ser Glu Arg Ile Asp Val Ile Ile Asp Phe Ser Gln
        290                 295                 300

Cys Asp Gly Asp Glu Ile Val Leu Lys Asn Asp Leu Gly Pro Asp Ala
305                 310                 315                 320

Asp Pro Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
                355                 360                 365

Leu Val Gly Ser Thr Asp Asp Phe Gly Arg Pro Leu Leu Leu Leu Asp
        370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 28
<211> LENGTH: 512
<212> TYPE: PRT
<213> ORGANISM: Bacillus wakoensis

<400> SEQUENCE: 28

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
```

```
                    85                  90                  95
Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Ser
                115                 120                 125

Phe Phe Lys Glu Glu Val Tyr Arg Tyr Leu Asn Glu Gln Arg Ala Met
        130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
                180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
        210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
                260                 265                 270

Gly Ser Asp Gly Gly Leu Leu Glu Lys Pro Val Gln Met Asn Lys Ile
            275                 280                 285

Pro Ile Glu Pro Ser Glu Arg Ile Asp Val Ile Ile Asp Phe Ser Gln
        290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
                340                 345                 350

Ile Arg Ser Leu Arg Asn Asn Lys Ile Ser Thr Ile Arg Asn Leu Lys
            355                 360                 365

Leu Val Gly Ser Thr Asp Asp Phe Gly Arg Pro Leu Leu Leu Leu Asn
        370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
                420                 425                 430

Leu Glu Arg Tyr Asn His Asp Gly Thr Ile Ile Tyr Thr Gly Pro Pro
            435                 440                 445

Arg Ala Pro Glu Pro Asn Glu Arg Gly Trp Lys Asp Thr Val Ser Ala
        450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510
```

<210> SEQ ID NO 29
<211> LENGTH: 512
<212> TYPE: PRT
<213> ORGANISM: Bacillus wakoensis

<400> SEQUENCE: 29

```
Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr Ile Arg Asn Leu Lys
        355                 360                 365

Leu Val Gly Ser Thr Asp Asp Phe Gly Arg Pro Leu Leu Leu Leu Asn
```

```
                370                 375                 380
Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
            435                 440                 445

Arg Pro Pro Glu Pro Asn Glu Arg Gly Trp Lys Asp Thr Val Ser Ala
            450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510

<210> SEQ ID NO 30
<211> LENGTH: 512
<212> TYPE: PRT
<213> ORGANISM: Bacillus wakoensis

<400> SEQUENCE: 30

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Thr Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240
```

```
Val Glu Pro Arg Lys Tyr Arg Phe Arg Ile Leu Asn Gly Ser Asn Thr
            245                 250                 255

Arg Ser Tyr Gln Leu His Leu Asp Ser Asn Gln Glu Val Tyr Gln Ile
        260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
            325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr Ile Arg Asn Leu Lys
        355                 360                 365

Leu Val Gly Ser Thr Asp Asp Phe Gly Arg Pro Leu Leu Leu Leu Asn
        370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
            405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
            485                 490                 495

Met Met Arg Pro Met Lys Val Ile Asp Pro Lys Gln Arg Lys Asp Lys
            500                 505                 510

<210> SEQ ID NO 31
<211> LENGTH: 512
<212> TYPE: PRT
<213> ORGANISM: Bacillus wakoensis

<400> SEQUENCE: 31

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
            85                  90                  95

Arg His Val Thr His Leu His Gly Gly Arg Thr Pro Trp Val Ser Asp
            100                 105                 110
```

Gly Tyr Pro Glu Ala Trp Tyr Thr Lys Asp Tyr Lys Glu Val Gly Ser
            115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
                180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Pro Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr Ile Arg Asn Leu Lys
        355                 360                 365

Leu Val Gly Ser Thr Asp Asp Phe Gly Arg Pro Leu Leu Leu Leu Asn
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 32
<211> LENGTH: 512

<212> TYPE: PRT
<213> ORGANISM: Bacillus wakoensis

<400> SEQUENCE: 32

```
Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Pro Ser Glu Arg Ile Asp Val Ile Ile Asp Phe Ser Gln
290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asn
370                 375                 380

Asn Lys Lys Trp Ala Asp Pro Thr Thr Glu Lys Pro Lys Val Gly Asp
385                 390                 395                 400
```

```
Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
                420                 425                 430

Leu Glu Arg Tyr Asn His Asp Gly Thr Ile Ile Tyr Thr Gly Pro Pro
                435                 440                 445

Arg Pro Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510
```

<210> SEQ ID NO 33
<211> LENGTH: 512
<212> TYPE: PRT
<213> ORGANISM: Bacillus wakoensis

<400> SEQUENCE: 33

```
Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
                20                  25                  30

Thr Glu Phe Lys Lys Lys Leu His Arg Asp Leu Pro Pro Thr Thr Leu
                35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Ser
                115                 120                 125

Phe Phe Lys Glu Glu Val Tyr Arg Tyr Leu Asn Glu Gln Arg Ala Met
            130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
                180                 185                 190

Asp Arg Thr Phe Asn Glu Asp Gly Ser Leu Phe Tyr Pro Thr Gly Pro
                195                 200                 205

Glu Asp Gly Gly Glu Asp Leu Pro Asn Pro Ser Ile Val Pro Ala Phe
            210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
```

```
              260                 265                 270
Gly Ser Asp Gly Gly Leu Leu Glu Lys Pro Val Gln Met Asn Lys Ile
        275                 280                 285

Pro Ile Glu Pro Ser Glu Arg Ile Asp Val Ile Ile Asp Phe Ser Gln
        290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
        340                 345                 350

Ile Arg Ser Leu Arg Asn Asn Lys Ile Ser Thr His Arg Asn Leu Lys
        355                 360                 365

Leu Val Gly Ser Thr Asp Asp Phe Gly Arg Pro Leu Leu Leu Leu Asn
        370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
                420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
        450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510

<210> SEQ ID NO 34
<211> LENGTH: 512
<212> TYPE: PRT
<213> ORGANISM: Bacillus wakoensis

<400> SEQUENCE: 34

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
                20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Ser
        115                 120                 125
```

```
Phe Phe Lys Glu Glu Val Tyr Arg Tyr Leu Asn Glu Gln Arg Ala Met
    130                 135                 140
Met Leu Trp Tyr His Asp His Thr Met Gly Ile Thr Arg Leu Asn Asn
145                 150                 155                 160
Tyr Ala Gly Leu Ala Gly Ala Tyr Ile Ile Arg Asp Lys His Glu Lys
                165                 170                 175
Ser Leu Asn Leu Pro Glu Gly Glu Tyr Glu Val Pro Leu Ile Ile Gln
            180                 185                 190
Asp Arg Thr Phe Asn Glu Asp Gly Ser Leu Phe Tyr Pro Thr Gly Pro
        195                 200                 205
Glu Asp Gly Gly Glu Asp Leu Pro Asn Pro Ser Ile Val Pro Ala Phe
210                 215                 220
Leu Gly Asp Thr Val Leu Val Asn Gly Lys Val Trp Pro Tyr Leu Glu
225                 230                 235                 240
Val Glu Pro Arg Lys Tyr Arg Phe Arg Ile Leu Asn Gly Ser Asn Thr
                245                 250                 255
Arg Ser Tyr Gln Leu His Leu Asp Ser Asn Gln Glu Val Tyr Gln Ile
            260                 265                 270
Gly Ser Asp Gly Gly Leu Leu Glu Lys Pro Val Gln Met Asn Lys Ile
        275                 280                 285
Pro Ile Glu Pro Ser Glu Arg Ile Asp Val Ile Ile Asp Phe Ser Gln
290                 295                 300
Cys Asp Gly Asp Glu Ile Val Leu Lys Asn Asp Leu Gly Pro Asp Ala
305                 310                 315                 320
Asp Pro Glu Asp Glu Thr Asn Glu Ile Met Lys Phe Lys Val Ser Lys
                325                 330                 335
Pro Leu Lys Glu Lys Asp Thr Ser Val Ile Pro Lys Arg Leu Ser Thr
            340                 345                 350
Ile Arg Ser Leu Arg Asn Asn Lys Ile Ser Thr His Arg Asn Leu Lys
        355                 360                 365
Leu Val Gly Ser Thr Asp Asp Phe Gly Arg Pro Leu Leu Leu Leu Asn
370                 375                 380
Asn Lys Lys Trp Ala Asp Pro Thr Thr Glu Lys Pro Lys Val Gly Asp
385                 390                 395                 400
Thr Glu Val Trp Ser Phe Ile Asn Thr Thr Asp Phe Ala His Pro Met
                405                 410                 415
His Ile His Leu Ile His Phe Gln Val Leu Asp Arg Gln Pro Phe Asp
            420                 425                 430
Leu Glu Arg Tyr Asn His Asp Gly Thr Ile Ile Tyr Thr Gly Pro Pro
        435                 440                 445
Arg Ala Pro Glu Pro Asn Glu Arg Gly Trp Lys Asp Thr Val Ser Ala
450                 455                 460
Pro Ala Gly Gln Ile Thr Arg Val Ile Gly Thr Phe Ala Pro Tyr Thr
465                 470                 475                 480
Gly Asn Tyr Val Trp His Cys His Ile Leu Glu His Glu Asp His Asp
                485                 490                 495
Met Met Arg Pro Met Lys Val Ile Asp Pro Lys Gln Arg Lys Asp Lys
            500                 505                 510
```

<210> SEQ ID NO 35
<211> LENGTH: 512
<212> TYPE: PRT
<213> ORGANISM: Bacillus wakoensis

<400> SEQUENCE: 35

```
Met Arg Arg Lys Leu Glu Lys Phe Val Asp Ser Leu Pro Ile Met Glu
  1               5                  10                  15

Thr Leu Gln Pro Lys Thr Lys Gly Lys Asn Tyr Tyr Glu Val Lys Ile
             20                  25                  30

Thr Glu Phe Lys Lys Lys Leu His Arg Asp Leu Pro Pro Thr Thr Leu
         35                  40                  45

Trp Gly Tyr Asn Ala Gln Phe Pro Gly Pro Thr Ile Glu Ala Asn Ser
     50                  55                  60

Asn Glu Pro Val Glu Val Lys Trp Ile Asn Glu Leu Pro Asn Lys His
 65                  70                  75                  80

Phe Leu Pro Val Asp Trp Ser Ile Met Asn Lys Asp Leu Pro Glu Val
                 85                  90                  95

Arg His Val Thr His Leu His Gly Gly Arg Thr Pro Trp Val Ser Asp
             100                 105                 110

Gly Tyr Pro Glu Ala Trp Tyr Thr Lys Asp Tyr Lys Glu Val Gly Ser
         115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                 165                 170                 175

Ser Leu Asn Leu Pro Glu Gly Glu Tyr Glu Val Pro Leu Ile Ile Gln
             180                 185                 190

Asp Arg Thr Phe Asn Glu Asp Gly Ser Leu Phe Tyr Pro Thr Gly Pro
         195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                 245                 250                 255

Arg Ser Tyr Gln Leu His Leu Asp Ser Asn Gln Glu Val Tyr Gln Ile
             260                 265                 270

Gly Ser Asp Gly Gly Leu Leu Glu Lys Pro Val Gln Met Asn Lys Ile
         275                 280                 285

Pro Ile Glu Ser Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                 325                 330                 335

Pro Leu Lys Glu Lys Asp Thr Ser Val Ile Pro Lys Arg Leu Ser Thr
             340                 345                 350

Ile Arg Ser Leu Arg Asn Asn Lys Ile Ser Thr His Arg Asn Leu Lys
         355                 360                 365

Leu Val Gly Ser Thr Asp Asp Phe Gly Arg Pro Leu Leu Leu Leu Asn
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                 405                 410                 415
```

```
His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Pro Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 36
<211> LENGTH: 512
<212> TYPE: PRT
<213> ORGANISM: Bacillus wakoensis

<400> SEQUENCE: 36

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
    210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285
```

```
Pro Ile Glu Ser Ser Glu Arg Ile Asp Val Ile Ile Asp Phe Ser Gln
         290                 295                 300

Cys Asp Gly Asp Glu Ile Val Leu Lys Asn Asp Leu Gly Pro Asp Ala
305                 310                 315                 320

Asp Pro Glu Asp Glu Thr Asn Glu Ile Met Lys Phe Lys Val Ser Lys
                 325                 330                 335

Pro Leu Lys Glu Lys Asp Thr Ser Val Ile Pro Lys Arg Leu Ser Thr
             340                 345                 350

Ile Arg Ser Leu Arg Asn Asn Lys Ile Ser Thr His Arg Asn Leu Lys
         355                 360                 365

Leu Val Gly Ser Thr Asp Asp Phe Gly Arg Pro Leu Leu Leu Leu Asn
     370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Asp Phe Ala His Pro Met
                 405                 410                 415

His Ile His Leu Ile His Phe Gln Val Leu Asp Arg Gln Pro Phe Asp
                 420                 425                 430

Leu Glu Arg Tyr Asn His Asp Gly Thr Ile Ile Tyr Thr Gly Pro Pro
         435                 440                 445

Arg Pro Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                 485                 490                 495

Met Met Arg Pro Met Lys Val Ile Asp Pro Lys Gln Arg Lys Asp Lys
             500                 505                 510

<210> SEQ ID NO 37
<211> LENGTH: 512
<212> TYPE: PRT
<213> ORGANISM: Bacillus wakoensis

<400> SEQUENCE: 37

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
             20                  25                  30

Thr Glu Phe Lys Lys Lys Leu His Arg Asp Leu Pro Pro Thr Thr Leu
         35                  40                  45

Trp Gly Tyr Asn Ala Gln Phe Pro Gly Pro Thr Ile Glu Ala Asn Ser
     50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                 85                  90                  95

Arg His Val Thr His Leu His Gly Gly Arg Thr Pro Trp Val Ser Asp
             100                 105                 110

Gly Tyr Pro Glu Ala Trp Tyr Thr Lys Asp Tyr Lys Glu Val Gly Ser
         115                 120                 125

Phe Phe Lys Glu Glu Val Tyr Arg Tyr Leu Asn Glu Gln Arg Ala Met
     130                 135                 140

Met Leu Trp Tyr His Asp His Thr Met Gly Ile Thr Arg Leu Asn Asn
```

```
                145                 150                 155                 160
        Tyr Ala Gly Leu Ala Gly Ala Tyr Ile Ile Arg Asp Lys His Glu Lys
                        165                 170                 175

Ser Leu Asn Leu Pro Glu Gly Glu Tyr Glu Val Pro Leu Ile Ile Gln
                        180                 185                 190

Asp Arg Thr Phe Asn Glu Asp Gly Ser Leu Phe Tyr Pro Thr Gly Pro
                        195                 200                 205

Glu Asp Gly Gly Glu Asp Leu Pro Asn Pro Ser Ile Val Pro Ala Phe
                        210                 215                 220

Leu Gly Asp Thr Val Leu Val Asn Gly Lys Val Trp Pro Tyr Leu Glu
        225                 230                 235                 240

Val Glu Pro Arg Lys Tyr Arg Phe Arg Ile Leu Asn Gly Ser Asn Thr
                        245                 250                 255

Arg Ser Tyr Gln Leu His Leu Asp Ser Asn Gln Glu Val Tyr Gln Ile
                        260                 265                 270

Gly Ser Asp Gly Gly Leu Leu Glu Lys Pro Val Gln Met Asn Lys Ile
                        275                 280                 285

Pro Ile Glu Ser Ser Glu Arg Ile Asp Val Ile Ile Asp Phe Ser Gln
                        290                 295                 300

Cys Asp Gly Asp Glu Ile Val Leu Lys Asn Asp Leu Gly Pro Asp Ala
        305                 310                 315                 320

Asp Pro Glu Asp Glu Thr Asn Glu Ile Met Lys Phe Lys Val Ser Lys
                        325                 330                 335

Pro Leu Lys Glu Lys Asp Thr Ser Val Ile Pro Lys Arg Leu Ser Thr
                        340                 345                 350

Ile Arg Ser Leu Arg Asn Asn Lys Ile Ser Thr His Arg Asn Leu Lys
                        355                 360                 365

Leu Val Gly Ser Thr Asp Asp Phe Gly Arg Pro Leu Leu Leu Leu Asn
                        370                 375                 380

Asn Lys Lys Trp Ala Asp Pro Thr Thr Glu Lys Pro Lys Val Gly Asp
        385                 390                 395                 400

Thr Glu Val Trp Ser Phe Ile Asn Thr Thr Asp Phe Ala His Pro Met
                        405                 410                 415

His Ile His Leu Ile His Phe Gln Val Leu Asp Arg Gln Pro Phe Asp
                        420                 425                 430

Leu Glu Arg Tyr Asn His Asp Gly Thr Ile Ile Tyr Thr Gly Pro Pro
                        435                 440                 445

Arg Ala Pro Glu Pro Asn Glu Arg Gly Trp Lys Asp Thr Val Ser Ala
        450                 455                 460

Pro Ala Gly Gln Ile Thr Arg Val Ile Gly Thr Phe Ala Pro Tyr Thr
        465                 470                 475                 480

Gly Asn Tyr Val Trp His Cys His Ile Leu Glu His Glu Asp His Asp
                        485                 490                 495

Met Met Arg Pro Met Lys Val Ile Asp Pro Lys Gln Arg Lys Asp Lys
                        500                 505                 510

<210> SEQ ID NO 38
<211> LENGTH: 512
<212> TYPE: PRT
<213> ORGANISM: Bacillus wakoensis

<400> SEQUENCE: 38

Met Arg Arg Lys Leu Glu Lys Phe Val Asp Ser Leu Pro Ile Met Glu
1               5                   10                  15
```

```
Thr Leu Gln Pro Lys Thr Lys Gly Lys Asn Tyr Tyr Glu Val Lys Ile
             20                  25                  30

Gln Glu Phe Lys Lys Lys Leu His Arg Asp Leu Pro Thr Thr Leu
         35                  40                  45

Trp Gly Tyr Asn Ala Gln Phe Pro Gly Pro Thr Ile Glu Ala Asn Ser
 50                  55                  60

Asn Glu Pro Val Glu Val Lys Trp Ile Asn Glu Leu Pro Asn Lys His
 65                  70                  75                  80

Phe Leu Pro Val Asp Trp Ser Ile Met Asn Lys Asp Leu Pro Glu Val
                 85                  90                  95

Arg His Val Thr His Leu His Gly Gly Arg Thr Pro Trp Val Ser Asp
             100                 105                 110

Gly Tyr Pro Glu Ala Trp Tyr Thr Lys Asp Tyr Lys Glu Val Gly Pro
         115                 120                 125

Phe Phe Lys Glu Glu Val Tyr Arg Tyr Leu Asn Glu Gln Arg Ala Met
 130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                 165                 170                 175

Ser Leu Asn Leu Pro Glu Gly Glu Tyr Glu Val Pro Leu Ile Ile Gln
             180                 185                 190

Asp Arg Thr Phe Asn Glu Asp Gly Ser Leu Phe Tyr Pro Thr Gly Pro
         195                 200                 205

Glu Asp Gly Gly Glu Asp Leu Pro Asn Pro Ser Ile Val Pro Ala Phe
 210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                 245                 250                 255

Arg Ser Tyr Gln Leu His Leu Asp Ser Asn Gln Glu Val Tyr Gln Ile
             260                 265                 270

Gly Ser Asp Gly Gly Leu Leu Glu Lys Pro Val Gln Met Asn Lys Ile
         275                 280                 285

Pro Ile Glu Ser Ser Glu Arg Ile Asp Val Ile Ile Asp Phe Ser Gln
 290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                 325                 330                 335

Pro Leu Lys Glu Lys Asp Thr Ser Val Ile Pro Lys Arg Leu Ser Thr
             340                 345                 350

Ile Arg Ser Leu Arg Asn Asn Lys Ile Ser Thr His Arg Asn Leu Lys
         355                 360                 365

Leu Val Gly Ser Thr Asp Asp Phe Gly Arg Pro Leu Leu Leu Asp
 370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                 405                 410                 415

His Ile His Leu Ile His Phe Gln Val Leu Asp Arg Gln Pro Phe Asp
             420                 425                 430

Leu Glu Arg Tyr Asn His Asp Gly Thr Ile Ile Tyr Thr Gly Pro Pro
```

```
                435                 440                 445
Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                    485                 490                 495

Met Met Arg Pro Met Lys Val Ile Asp Pro Lys Gln Arg Lys Asp Lys
                500                 505                 510

<210> SEQ ID NO 39
<211> LENGTH: 512
<212> TYPE: PRT
<213> ORGANISM: Bacillus wakoensis

<400> SEQUENCE: 39

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Pro
        115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Glu Arg Ile Asp Val Ile Asp Phe Ser Gln
290                 295                 300
```

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
            325                 330                 335

Pro Leu Lys Glu Lys Asp Thr Ser Val Ile Pro Lys Arg Leu Ser Thr
        340                 345                 350

Ile Arg Ser Leu Arg Asn Asn Lys Ile Ser Thr Ile Arg Asn Leu Lys
    355                 360                 365

Leu Val Gly Ser Thr Asp Asp Phe Gly Arg Pro Leu Leu Leu Leu Asp
370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
                420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510

<210> SEQ ID NO 40
<211> LENGTH: 512
<212> TYPE: PRT
<213> ORGANISM: Bacillus wakoensis

<400> SEQUENCE: 40

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Pro
            115                 120                 125

Phe Phe Lys Glu Glu Val Tyr Arg Tyr Leu Asn Glu Gln Arg Ala Met
        130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

```
Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Pro Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr Ile Arg Asn Leu Lys
        355                 360                 365

Leu Val Gly Ser Thr Asp Asp Phe Gly Arg Pro Leu Leu Leu Leu Asp
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Ala Pro Glu Pro Asn Glu Arg Gly Trp Lys Asp Thr Val Ser Ala
450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 41
<211> LENGTH: 512
<212> TYPE: PRT
<213> ORGANISM: Bacillus wakoensis

<400> SEQUENCE: 41

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
```

```
                35                  40                  45
Trp Gly Tyr Asn Ala Gln Phe Pro Gly Pro Thr Ile Glu Ala Asn Ser
 50                  55                  60

Asn Glu Pro Val Glu Val Lys Trp Ile Asn Glu Leu Pro Asn Lys His
 65                  70                  75                  80

Phe Leu Pro Val Asp Trp Ser Ile Met Asn Lys Asp Leu Pro Glu Val
                 85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Pro
                115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
                180                 185                 190

Asp Arg Thr Phe Asn Glu Asp Gly Ser Leu Phe Tyr Pro Thr Gly Pro
                195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
                260                 265                 270

Gly Ser Asp Gly Gly Leu Leu Glu Lys Pro Val Gln Met Asn Lys Ile
                275                 280                 285

Pro Ile Glu Pro Ser Glu Arg Ile Asp Val Ile Ile Asp Phe Ser Gln
290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
                340                 345                 350

Ile Arg Ser Leu Arg Asn Asn Lys Ile Ser Thr Ile Arg Asn Leu Lys
                355                 360                 365

Leu Val Gly Ser Thr Asp Asp Phe Gly Arg Pro Leu Leu Leu Leu Asp
                370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
                420                 425                 430

Leu Glu Arg Tyr Asn His Asp Gly Thr Ile Ile Tyr Thr Gly Pro Pro
                435                 440                 445

Arg Pro Pro Glu Pro Asn Glu Arg Gly Trp Lys Asp Thr Val Ser Ala
450                 455                 460
```

```
Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                    485                 490                 495

Met Met Arg Pro Met Lys Val Ile Asp Pro Lys Gln Arg Lys Asp Lys
                500                 505                 510

<210> SEQ ID NO 42
<211> LENGTH: 512
<212> TYPE: PRT
<213> ORGANISM: Bacillus wakoensis

<400> SEQUENCE: 42

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
                20                  25                  30

Thr Glu Phe Lys Lys Leu His Arg Asp Leu Pro Pro Thr Thr Leu
            35                  40                  45

Trp Gly Tyr Asn Ala Gln Phe Pro Gly Pro Thr Ile Glu Ala Asn Ser
50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
                100                 105                 110

Gly Tyr Pro Glu Ala Trp Tyr Thr Lys Asp Tyr Lys Glu Val Gly Pro
            115                 120                 125

Phe Phe Lys Glu Glu Val Tyr Arg Tyr Leu Asn Glu Gln Arg Ala Met
130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
            275                 280                 285

Pro Ile Glu Pro Ser Glu Arg Ile Asp Val Ile Ile Asp Phe Ser Gln
            290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
```

```
                    325                 330                 335
Pro Leu Lys Glu Lys Asp Thr Ser Val Ile Pro Lys Arg Leu Ser Thr
                340                 345                 350
Ile Arg Ser Leu Arg Asn Asn Lys Ile Ser Thr Ile Arg Asn Leu Lys
                355                 360                 365
Leu Val Gly Ser Thr Asp Asp Phe Gly Arg Pro Leu Leu Leu Leu Asp
                370                 375                 380
Asn Lys Lys Trp Ala Asp Pro Thr Thr Glu Lys Pro Lys Val Gly Asp
385                 390                 395                 400
Thr Glu Val Trp Ser Phe Ile Asn Thr Thr Asp Phe Ala His Pro Met
                    405                 410                 415
His Ile His Leu Ile His Phe Gln Val Leu Asp Arg Gln Pro Phe Asp
                420                 425                 430
Leu Glu Arg Tyr Asn His Asp Gly Thr Ile Ile Tyr Thr Gly Pro Pro
                435                 440                 445
Arg Pro Pro Glu Pro Asn Glu Arg Gly Trp Lys Asp Thr Val Ser Ala
450                 455                 460
Pro Ala Gly Gln Ile Thr Arg Val Ile Gly Thr Phe Ala Pro Tyr Thr
465                 470                 475                 480
Gly Asn Tyr Val Trp His Cys His Ile Leu Glu His Glu Asp His Asp
                    485                 490                 495
Met Met Arg Pro Met Lys Val Ile Asp Pro Lys Gln Arg Lys Asp Lys
                500                 505                 510

<210> SEQ ID NO 43
<211> LENGTH: 512
<212> TYPE: PRT
<213> ORGANISM: Bacillus wakoensis

<400> SEQUENCE: 43

Met Arg Arg Lys Leu Glu Lys Phe Val Asp Ser Leu Pro Ile Met Glu
1               5                   10                  15
Thr Leu Gln Pro Lys Thr Lys Gly Lys Asn Tyr Tyr Glu Val Lys Ile
                20                  25                  30
Thr Glu Phe Lys Lys Leu His Arg Asp Leu Pro Pro Thr Thr Leu
                35                  40                  45
Trp Gly Tyr Asn Ala Gln Phe Pro Gly Pro Thr Ile Glu Ala Asn Ser
        50                  55                  60
Asn Glu Pro Val Glu Val Lys Trp Ile Asn Glu Leu Pro Asn Lys His
65                  70                  75                  80
Phe Leu Pro Val Asp Trp Ser Ile Met Asn Lys Asp Leu Pro Glu Val
                85                  90                  95
Arg His Val Thr His Leu His Gly Gly Arg Thr Pro Trp Val Ser Asp
                100                 105                 110
Gly Tyr Pro Glu Ala Trp Tyr Thr Lys Asp Tyr Lys Glu Val Gly Pro
            115                 120                 125
Phe Phe Lys Glu Glu Val Tyr Arg Tyr Leu Asn Glu Gln Arg Ala Met
        130                 135                 140
Met Leu Trp Tyr His Asp His Thr Met Gly Ile Thr Arg Leu Asn Asn
145                 150                 155                 160
Tyr Ala Gly Leu Ala Gly Ala Tyr Ile Ile Arg Asp Lys His Glu Lys
                165                 170                 175
Ser Leu Asn Leu Pro Glu Gly Glu Tyr Glu Val Pro Leu Ile Ile Gln
                180                 185                 190
```

```
Asp Arg Thr Phe Asn Glu Asp Gly Ser Leu Phe Tyr Pro Thr Gly Pro
            195                 200                 205

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Ala Ser Asn Thr
                245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Pro Ser Glu Arg Ile Asp Val Ile Ile Asp Phe Ser Gln
    290                 295                 300

Cys Asp Gly Asp Glu Ile Val Leu Lys Asn Asp Leu Gly Pro Asp Ala
305                 310                 315                 320

Asp Pro Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
            340                 345                 350

Ile Arg Ser Leu Arg Asn Asn Lys Ile Ser Thr Ile Arg Asn Leu Lys
        355                 360                 365

Leu Val Gly Ser Thr Asp Asp Phe Gly Arg Pro Leu Leu Leu Leu Asp
    370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
        435                 440                 445

Arg Pro Pro Glu Pro Asn Glu Arg Gly Trp Lys Asp Thr Val Ser Ala
    450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
            500                 505                 510

<210> SEQ ID NO 44
<211> LENGTH: 507
<212> TYPE: PRT
<213> ORGANISM: Bacillus salsus

<400> SEQUENCE: 44

Met Ser Pro Lys Leu Glu Lys Phe Val Asp Gln Leu Pro Ile Leu Ala
1               5                   10                  15

Ala Leu Lys Pro Asn Arg Arg Glu Ala Asp Gly Asp Tyr Tyr Glu Ile
            20                  25                  30

Thr Met Glu Glu Phe Phe Gln Lys Leu His Arg Asp Leu Pro Pro Thr
        35                  40                  45

Arg Leu Trp Gly Tyr Asn Arg Gln Val Pro Gly Pro Thr Leu Asp Val
    50                  55                  60
```

-continued

```
Ile Gln Asp Glu Pro Ile Lys Val Lys Trp Val Asn Asn Leu Pro Ser
 65                  70                  75                  80

Arg His Phe Leu Pro Val Asp Lys Ser Phe Leu Met Pro Asp Leu Pro
                 85                  90                  95

Glu Val Arg Thr Val Thr His Leu His Gly Glu Thr Pro Pro Pro
            100                 105                 110

Ser Asp Gly Tyr Pro Glu Ala Trp Phe Thr Arg Asn Tyr Ala Glu Val
            115                 120                 125

Gly Pro Phe Phe Glu Arg Glu Val Tyr Glu Tyr Leu Asn Gln Gln Arg
            130                 135                 140

Ala Thr Met Leu Trp Tyr His Asp His Ala Met Gly Thr Thr Arg Leu
145                 150                 155                 160

Asn Asn Tyr Ala Gly Leu Ala Gly Ala Tyr Ile Ile Arg Asp Lys Tyr
                165                 170                 175

Glu Lys Ser Leu Asn Leu Pro Ser Gly Glu Tyr Glu Ile Pro Leu Ile
            180                 185                 190

Ile Gln Asp Lys Ser Phe Asn Arg Asp Gly Ser Leu Ser Tyr Pro Lys
            195                 200                 205

Gln Pro Asp Asn Ala Ser Glu Asp Leu Pro Asn Pro Ser Val Val Pro
            210                 215                 220

Ala Phe Phe Gly Asp Thr Ile Leu Val Asn Gly Lys Val Trp Pro Phe
225                 230                 235                 240

Leu Lys Val Glu Pro Arg Lys Tyr Arg Phe Arg Met Leu Asn Ala Ser
                245                 250                 255

Asn Thr Arg Gly Tyr Gln Leu His Leu Asp Ser Glu Gln Pro Phe Tyr
                260                 265                 270

Gln Ile Gly Ser Asp Gly Gly Leu Leu Glu Lys Pro Val Lys Leu Asn
            275                 280                 285

Met Ile Thr Ile Glu Pro Ser Glu Arg Met Asp Ile Ile Leu Asp Phe
            290                 295                 300

Ser Lys Tyr Glu Gly Lys Asp Ile Ile Leu Arg Asn Asn Leu Gly Pro
305                 310                 315                 320

Asn Ala Asp Pro Glu Asn Glu Thr Asp Glu Val Met Lys Phe Ile Val
                325                 330                 335

Ser Lys Pro Leu Lys Glu Gln Asp Lys Ser Val Ile Pro Lys Arg Leu
            340                 345                 350

Ser Thr Ile Pro Ser Leu Arg Ala Asn Gln Ile Ser Ala Tyr Arg Asn
            355                 360                 365

Leu Lys Leu Val Gly Ser Gln Asp Glu Tyr Gly Arg Pro Leu Leu Leu
            370                 375                 380

Leu Asn Asn Lys Arg Trp Ala Asp Pro Ile Thr Glu Lys Pro Arg Leu
385                 390                 395                 400

Gly Thr Thr Glu Ile Trp Ser Phe Ile Asn Thr Thr Ala Phe Ala His
                405                 410                 415

Pro Met His Ile His Leu Ile Gln Phe Gln Val Leu Glu Arg Gln Pro
                420                 425                 430

Phe Asp Leu Asp Arg Tyr Asn Glu Asp Gly Gln Ile Ile Phe Thr Gly
            435                 440                 445

Ala Pro Lys Pro Pro Glu Pro Asn Glu Arg Gly Trp Lys Asp Thr Ile
            450                 455                 460

Lys Ala Thr Ser Gly His Ile Thr Arg Val Ile Gly Lys Tyr Gly Pro
465                 470                 475                 480
```

```
Phe Thr Gly Asn Tyr Val Trp His Cys His Ile Leu Glu His Glu Asp
            485                 490                 495

His Asp Met Met Arg Pro Phe Lys Val Ile Glu
        500                 505

<210> SEQ ID NO 45
<211> LENGTH: 24
<212> TYPE: DNA
<213> ORGANISM: artificial sequence
<220> FEATURE:
<223> OTHER INFORMATION: primer

<400> SEQUENCE: 45
gaaattaata cgactcacta tagg                                              24

<210> SEQ ID NO 46
<211> LENGTH: 27
<212> TYPE: DNA
<213> ORGANISM: artificial sequence
<220> FEATURE:
<223> OTHER INFORMATION: primer

<400> SEQUENCE: 46
ggttatgcta gttattgctc agcggtg                                           27

<210> SEQ ID NO 47
<211> LENGTH: 30
<212> TYPE: DNA
<213> ORGANISM: Bacillus spec

<400> SEQUENCE: 47
attcagaata cgaaaacgat atttacgcgg                                        30

<210> SEQ ID NO 48
<211> LENGTH: 35
<212> TYPE: DNA
<213> ORGANISM: Bacillus spec

<400> SEQUENCE: 48
atcgttttcg tattctgaat gctagcaaca cccgt                                  35

<210> SEQ ID NO 49
<211> LENGTH: 30
<212> TYPE: DNA
<213> ORGANISM: Bacillus spec

<400> SEQUENCE: 49
gcccacttct ttataatctt tcgtatacca                                        30

<210> SEQ ID NO 50
<211> LENGTH: 35
<212> TYPE: DNA
<213> ORGANISM: Bacillus spec

<400> SEQUENCE: 50
aagattataa agaagtgggc cccttcttca agaa                                   35

<210> SEQ ID NO 51
<211> LENGTH: 30
<212> TYPE: DNA
<213> ORGANISM: Bacillus spec

<400> SEQUENCE: 51
cagcagcagc agaggacgac caaaatcatc                                        30
```

<210> SEQ ID NO 52
<211> LENGTH: 35
<212> TYPE: DNA
<213> ORGANISM: Bacillus spec

<400> SEQUENCE: 52
gtcgtcctct gctgctgctg gacaacaaaa aatgg                      35

<210> SEQ ID NO 53
<211> LENGTH: 30
<212> TYPE: DNA
<213> ORGANISM: Bacillus spec

<400> SEQUENCE: 53
ggtgctaatt ttgttattac gcaggctacg                            30

<210> SEQ ID NO 54
<211> LENGTH: 35
<212> TYPE: DNA
<213> ORGANISM: Bacillus spec

<400> SEQUENCE: 54
gtaataacaa aattagcacc attcgtaatc tgaaa                      35

<210> SEQ ID NO 55
<211> LENGTH: 30
<212> TYPE: DNA
<213> ORGANISM: Bacillus spec

<400> SEQUENCE: 55
ttcaatcgga attttgttca tctgcaccgg                            30

<210> SEQ ID NO 56
<211> LENGTH: 35
<212> TYPE: DNA
<213> ORGANISM: Bacillus spec

<400> SEQUENCE: 56
tgaacaaaat tccgattgaa cccagcgaac gcatt                      35

<210> SEQ ID NO 57
<211> LENGTH: 30
<212> TYPE: DNA
<213> ORGANISM: Bacillus spec

<400> SEQUENCE: 57
acgaggcgga ccggtataga taatggtgcc                            30

<210> SEQ ID NO 58
<211> LENGTH: 35
<212> TYPE: DNA
<213> ORGANISM: Bacillus spec

<400> SEQUENCE: 58
tctataccgg tccgcctcgt ccaccggaac cgaat                      35

<210> SEQ ID NO 59
<211> LENGTH: 30
<212> TYPE: DNA
<213> ORGANISM: Bacillus spec

<400> SEQUENCE: 59

```
gattttcacc tcataatagt ttttgccttt                                       30
```

<210> SEQ ID NO 60
<211> LENGTH: 35
<212> TYPE: DNA
<213> ORGANISM: Bacillus spec

<400> SEQUENCE: 60

```
actattatga ggtgaaaatc acagagttta aaaaa                                 35
```

<210> SEQ ID NO 61
<211> LENGTH: 30
<212> TYPE: DNA
<213> ORGANISM: Bacillus spec

<400> SEQUENCE: 61

```
atctgcatcc ggacccagat cattttttcag                                      30
```

<210> SEQ ID NO 62
<211> LENGTH: 35
<212> TYPE: DNA
<213> ORGANISM: Bacillus spec

<400> SEQUENCE: 62

```
atctgggtcc ggatgcagat cccgaagatg aaacc                                 35
```

<210> SEQ ID NO 63
<211> LENGTH: 13
<212> TYPE: PRT
<213> ORGANISM: artificial sequence
<220> FEATURE:
<223> OTHER INFORMATION: primer

<400> SEQUENCE: 63

Met Arg Arg Lys Leu Glu Lys Phe Val Asp Ser Leu Pro
1               5                   10

<210> SEQ ID NO 64
<211> LENGTH: 11
<212> TYPE: PRT
<213> ORGANISM: artificial sequence
<220> FEATURE:
<223> OTHER INFORMATION: primer

<400> SEQUENCE: 64

Met Arg Arg Lys Lys Phe Val Asp Ser Leu Pro
1               5                   10

<210> SEQ ID NO 65
<211> LENGTH: 509
<212> TYPE: PRT
<213> ORGANISM: Bacillus clausii

<400> SEQUENCE: 65

Met Glu Leu Glu Lys Phe Val Asp Pro Met Pro Ile Met Lys Thr Ala
1               5                   10                  15

Ile Pro Lys Lys Thr Ser Lys Asp Gly Asp Tyr Tyr Glu Ile Glu Met
            20                  25                  30

Lys Glu Phe Ser Gln Lys Leu His Arg Asp Leu Asn Pro Thr Arg Leu
        35                  40                  45

Trp Gly Tyr Asp Gly Gln Phe Pro Gly Pro Thr Ile Glu Val Met Arg
    50                  55                  60

Gly Lys Pro Ala Arg Ile Lys Trp Met Asn Asn Leu Pro Asp Thr His

-continued

```
                65                  70                  75                  80
Phe Leu Pro Ile Asp Arg Ser Ile His His Val Ala His Glu Pro Glu
                    85                  90                  95
Val Arg Thr Val Val His Leu His Gly Ser Glu Thr Thr Pro Ala Ser
                100                 105                 110
Asp Gly Tyr Pro Glu Ala Trp Phe Thr Lys Asp Phe Ala Glu Val Gly
                115                 120                 125
Ser Phe Phe Glu Gln Glu Thr Tyr Glu Tyr Pro Asn Asp Gln Arg Ala
                130                 135                 140
Ala Thr Leu Trp Tyr His Asp His Ala Met Gly Ile Thr Arg Leu Asn
145                 150                 155                 160
Val Tyr Ala Gly Leu Ser Gly Leu Tyr Ile Ile Arg Asp Pro Arg Glu
                165                 170                 175
Glu Gln Leu Asn Leu Pro Lys Gly Glu Phe Asp Ile Pro Leu Leu Ile
                180                 185                 190
Gln Asp Arg Ser Phe Asn Asp Asp Gly Ser Leu Phe Tyr Pro Ala Gln
                195                 200                 205
Pro Ala Asn Pro Ala Pro Asn Leu Pro Asn Pro Ser Val Leu Pro Phe
                210                 215                 220
Phe Val Gly Asp Thr Ile Leu Val Asn Gly Lys Val Trp Pro Tyr Leu
225                 230                 235                 240
Gln Val Glu Pro Arg Lys Tyr Arg Phe Arg Ile Leu Asn Gly Ser Asn
                245                 250                 255
Ser Arg Ser Tyr Gln Leu Ala Leu Asp Ser Glu Ala Pro Phe Tyr Gln
                260                 265                 270
Ile Ala Ser Asp Gly Gly Leu Leu Arg Arg Thr Val Ser Leu Gln Ala
                275                 280                 285
Phe Asp Ile Arg Pro Ala Glu Arg Ile Glu Ala Ile Ile Asp Phe Ser
                290                 295                 300
Lys Phe Glu Gly Gln Thr Ile Thr Leu Lys Asn Asn Ala Ser Thr Asp
305                 310                 315                 320
Ala Thr Ala Asp Val Met Gln Phe Gln Val Val Leu Pro Leu Ser Gly
                325                 330                 335
Glu Asp Thr Ser Ile Ile Pro Gln Asn Leu Ser Tyr Ile Pro Ser Leu
                340                 345                 350
Gln Gln Asn Asp Val Lys Arg Ile Arg Asn Leu Lys Ile Ser Gly Thr
                355                 360                 365
Thr Asp Glu Tyr Gly Arg Pro Leu Leu Leu Leu Asn Asn Lys Leu Trp
                370                 375                 380
Ser Asp Pro Val Glu Glu Lys Pro Cys Leu Gly Thr Thr Glu Ile Trp
385                 390                 395                 400
Ser Phe Val Asn Val Thr Asn Val Pro His Pro Met His Ile His Leu
                405                 410                 415
Val Gln Phe Gln Leu Leu Asp His Arg Ala Phe Asn Val Glu Leu Tyr
                420                 425                 430
Asn Glu Asn Gly Gln Ile Glu Leu Val Gly Pro Thr Ile Pro Pro Lys
                435                 440                 445
Ile Asn Glu Arg Gly Trp Lys Asp Thr Ile Thr Ala Pro Ala Gly Gln
                450                 455                 460
Ile Thr Arg Val Ile Ala Arg Phe Ala Pro Phe Ser Gly Tyr Tyr Val
465                 470                 475                 480
Trp His Cys His Ile Leu Glu His Glu Asp Tyr Asp Met Met Arg Pro
                485                 490                 495
```

Phe Val Val Ile Asp Pro Lys Thr Glu Lys Glu Arg Arg
            500                 505

<210> SEQ ID NO 66
<211> LENGTH: 513
<212> TYPE: PRT
<213> ORGANISM: Bacillus subtilis

<400> SEQUENCE: 66

Met Thr Leu Glu Lys Phe Val Asp Ala Leu Pro Ile Pro Asp Thr Leu
1               5                   10                  15

Lys Pro Val Gln Gln Thr Thr Glu Lys Thr Tyr Tyr Glu Val Thr Met
            20                  25                  30

Glu Glu Cys Ala His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Glu
                85                  90                  95

Glu Pro Glu Val Lys Thr Val His Leu His Gly Gly Val Thr Pro
            100                 105                 110

Pro Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Thr Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Gly Pro Glu Asn Pro Ser Pro Ser Leu Pro Lys Pro Ser Ile
    210                 215                 220

Val Pro Ala Phe Cys Gly Asp Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Ala Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile Gln Asn

```
                355                 360                 365
Ile Arg Thr Leu Lys Leu Ala Gly Thr Gln Asp Glu Tyr Gly Arg Val
370                 375                 380

Val Gln Leu Leu Asn Asn Lys Arg Trp His Asp Pro Val Thr Glu Ala
385                 390                 395                 400

Pro Lys Ala Gly Thr Thr Glu Ile Trp Ser Ile Val Asn Pro Thr Gln
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Arg Gly Glu Leu Ser
                435                 440                 445

Tyr Thr Gly Pro Ala Val Pro Pro Pro Ser Glu Lys Gly Trp Lys
                450                 455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
                500                 505                 510

Lys

<210> SEQ ID NO 67
<211> LENGTH: 519
<212> TYPE: PRT
<213> ORGANISM: Escherichia coli

<400> SEQUENCE: 67

Met Gln Arg Arg Asp Phe Leu Lys Tyr Ser Val Ala Leu Gly Val Ala
1               5                   10                  15

Ser Ala Leu Pro Leu Trp Asn Arg Ala Val Phe Ala Ala Glu Arg Pro
                20                  25                  30

Thr Leu Pro Ile Pro Asp Leu Leu Thr Thr Asp Ala Arg Asn Arg Ile
                35                  40                  45

Gln Leu Thr Ile Gly Ala Gly Gln Ser Thr Phe Gly Gly Lys Thr Ala
50                  55                  60

Thr Thr Trp Gly Tyr Asn Gly Asn Leu Leu Gly Pro Ala Val Lys Leu
65                  70                  75                  80

Gln Arg Gly Lys Ala Val Thr Val Asp Ile Tyr Asn Gln Leu Thr Glu
                85                  90                  95

Glu Thr Thr Leu His Trp His Gly Leu Glu Val Pro Gly Glu Val Asp
                100                 105                 110

Gly Gly Pro Gln Gly Ile Ile Pro Pro Gly Gly Lys Arg Ser Val Thr
                115                 120                 125

Leu Asn Val Asp Gln Pro Ala Ala Thr Cys Trp Phe His Pro His Gln
130                 135                 140

His Gly Lys Thr Gly Arg Gln Val Ala Met Gly Leu Ala Gly Leu Val
145                 150                 155                 160

Val Ile Glu Asp Asp Glu Ile Leu Lys Leu Met Leu Pro Lys Gln Trp
                165                 170                 175

Gly Ile Asp Asp Val Pro Val Ile Val Gln Asp Lys Lys Phe Ser Ala
                180                 185                 190

Asp Gly Gln Ile Asp Tyr Gln Leu Asp Val Met Thr Ala Ala Val Gly
                195                 200                 205

Trp Phe Gly Asp Thr Leu Leu Thr Asn Gly Ala Ile Tyr Pro Gln His
```

-continued

```
            210                 215                 220
Ala Ala Pro Arg Gly Trp Leu Arg Leu Leu Asn Gly Cys Asn
225                 230                 235                 240

Ala Arg Ser Leu Asn Phe Ala Thr Ser Asp Asn Arg Pro Leu Tyr Val
                245                 250                 255

Ile Ala Ser Asp Gly Gly Leu Leu Pro Glu Pro Val Lys Val Ser Glu
                260                 265                 270

Leu Pro Val Leu Met Gly Glu Arg Phe Glu Val Leu Val Glu Val Asn
                275                 280                 285

Asp Asn Lys Pro Phe Asp Leu Val Thr Leu Pro Val Ser Gln Met Gly
            290                 295                 300

Met Ala Ile Ala Pro Phe Asp Lys Pro His Pro Val Met Arg Ile Gln
305                 310                 315                 320

Pro Ile Ala Ile Ser Ala Ser Gly Ala Leu Pro Asp Thr Leu Ser Ser
                325                 330                 335

Leu Pro Ala Leu Pro Ser Leu Glu Gly Leu Thr Val Arg Lys Leu Gln
                340                 345                 350

Leu Ser Met Asp Pro Met Leu Asp Met Met Gly Met Gln Met Leu Met
            355                 360                 365

Glu Lys Tyr Gly Asp Gln Ala Met Ala Gly Met Asp His Ser Gln Met
    370                 375                 380

Met Gly His Met Gly His Gly Asn Met Asn His Met Asn His Gly Gly
385                 390                 395                 400

Lys Phe Asp Phe His His Ala Asn Lys Ile Asn Gly Gln Ala Phe Asp
                405                 410                 415

Met Asn Lys Pro Met Phe Ala Ala Lys Gly Gln Tyr Glu Arg Trp
            420                 425                 430

Val Ile Ser Gly Val Gly Asp Met Met Leu His Pro Phe His Ile His
            435                 440                 445

Gly Thr Gln Phe Arg Ile Leu Ser Glu Asn Gly Lys Pro Pro Ala Ala
    450                 455                 460

His Arg Ala Gly Trp Lys Asp Thr Val Lys Val Glu Gly Asn Val Ser
465                 470                 475                 480

Glu Val Leu Val Lys Phe Asn His Asp Ala Pro Lys Glu His Ala Tyr
                485                 490                 495

Met Ala His Cys His Leu Leu Glu His Glu Asp Thr Gly Met Met Leu
            500                 505                 510

Gly Phe Thr Val Ser Asp Pro
            515
```